United States Patent
Koul et al.

(10) Patent No.: US 9,073,860 B2
(45) Date of Patent: Jul. 7, 2015

(54) AROMATIC AMIDES AS POTENTIATORS OF BIOEFFICACY OF ANTI-INFECTIVE DRUGS

(71) Applicant: COUNCIL OF SCIENTIFIC AND INDUSTRIAL RESEARCH, New Delhi (IN)

(72) Inventors: Surrinder Koul, Jammu Tawi (IN); Jawahir Lal Koul, Jammu Tawi (IN); Subhash Chandra Taneja, Jammu Tawi (IN); Pankaj Gupta, Jammu Tawi (IN); Inshad Ali Khan, Jammu Tawi (IN); Zahid Mehmood Mirza, Jammu Tawi (IN); Ashwani Kumar, Jammu Tawi (IN); Rakesh Kamal Johri, Jammu Tawi (IN); Monika Pandita, Jammu Tawi (IN); Anita Khosa, Jammu Tawi (IN); Ashok Kumar Tikoo, Jammu Tawi (IN); Subhash Chander Sharma, Jammu Tawi (IN); Vijeshwar Verma, Jammu Tawi (IN); Ghulam Nabi Qazi, Jammu Tawi (IN)

(73) Assignee: COUNCIL OF SCIENTIFIC AND INDUSTRIAL RESEARCH, New Delhi (IN)

( * ) Notice: Subject to any disclaimer, the term of this patent is extended or adjusted under 35 U.S.C. 154(b) by 92 days.

(21) Appl. No.: 14/051,671

(22) Filed: Oct. 11, 2013

(65) Prior Publication Data

US 2014/0073595 A1 Mar. 13, 2014

Related U.S. Application Data

(62) Division of application No. 11/391,391, filed on Mar. 29, 2006, now Pat. No. 8,580,752.

(30) Foreign Application Priority Data

Mar. 31, 2005 (IN) ........................... 0718/DEL/2005

(51) Int. Cl.
| | |
|---|---|
| C07D 211/46 | (2006.01) |
| A61K 31/351 | (2006.01) |
| C07D 295/108 | (2006.01) |
| C07D 311/58 | (2006.01) |
| C07D 317/60 | (2006.01) |
| C07D 319/18 | (2006.01) |
| A61K 31/445 | (2006.01) |
| A61K 31/4525 | (2006.01) |
| A61K 31/453 | (2006.01) |
| A61K 31/496 | (2006.01) |
| A61K 31/7036 | (2006.01) |
| C07D 319/16 | (2006.01) |

(52) U.S. Cl.
CPC .......... *C07D 211/46* (2013.01); *C07D 295/108* (2013.01); *C07D 311/58* (2013.01); *C07D 317/60* (2013.01); *C07D 319/18* (2013.01); *A61K 31/351* (2013.01); *A61K 31/445* (2013.01); *A61K 31/4525* (2013.01); *A61K 31/453* (2013.01); *A61K 31/496* (2013.01); *A61K 31/7036* (2013.01); *C07D 319/16* (2013.01)

(58) Field of Classification Search
None
See application file for complete search history.

(56) References Cited

U.S. PATENT DOCUMENTS

| | | | |
|---|---|---|---|
| 4,778,804 | A | 10/1988 | Okamoto et al. |
| 4,863,926 | A | 9/1989 | Okamoto et al. |
| 7,119,075 | B2 | 10/2006 | Qazi et al. |
| 2004/0198672 | A1 | 10/2004 | Qazi et al. |

OTHER PUBLICATIONS

Rebuffat et al., "Application of (1,1,1,2,2,3,3-heptafluoro-7,7-dimethyl-4,6-octanedionato) praseodymium induced paramagnetic shifts to the conformational study of methyl 2-cis, 4-trans-4methyl-5-phenylpentadienoates and Me 2-trans, 4- rans-methyl-5-phenylpentadienoates.", Bulletin de la Societe Chimique de France, 12, Pt. 2 (CAPLUS abstract)., 1974, pp. 2892-2894.

Vincent Gandon et al., "New transformations from a 3-silyloxy-2-aza-1, 3-diene: consecutive Zr-mediated retro-Brook rearrangement and reactions with electrophiles.", TETRAHEDRON, vol. 56, No. 26, Elsevier Science Ltd. (CAPLUS abstract)., 2000, pp. 4467-4472.

Takeaki Mitsudo et al., "Ruthenium complex-catalyzed highly selective codimeriztion of acetylenes and alkenes", Journal of the Chemical Society, Chemical Communications, vol. 8, (CAPLUS abstract)., 1991, pp. 598-599.

Sylvie Rebuffat et al., "N 567.—Application des deplacements paramagnetiques induits par Pr(fod)3 a l'etude conformationnelle des esters methyliques des acides methyl-4 phenyl-5 pentadiene-2 cis, 4 trans et-2 trans, 4 trans oiques",, Laboratoire de chimie appliquee aux corps organises. Museum National d'Histoire Naturelle, 63, rue Buffon, 75005 Paris, Jun. 27, 1974, pp. 2892-2894.

*Primary Examiner* — Yevegeny Valenrod
(74) *Attorney, Agent, or Firm* — Greenblum & Bernstein, P.L.C.

(57) ABSTRACT

The present invention relates to an aromatic substituted pentadienoic acid amides and there use in combination of specific amounts of aromatic amides i.e. 4-alkyl-5-(substituted phenyl)-2 (E),4(E)-pentadienoic acid amides, its geometrical isomers or their dihydro or tetrahydro derivatives and an anti-infective drug useful in potentiating the bioefficacy of antiinfective drug. The combination of the present invention is useful in the treatment of certain infections and disease at lower concentration of anti-infectives necessary to inhibit the growth of microbial strains and may also find applications in reducing the resistance in microorganisms.

22 Claims, 1 Drawing Sheet

Figure-IA
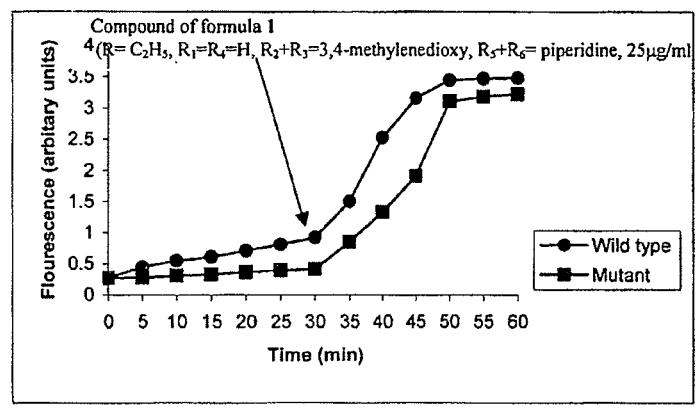
Figure-IB
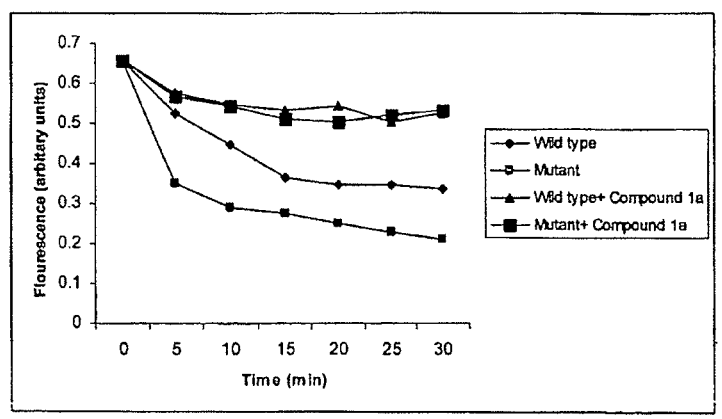

AROMATIC AMIDES AS POTENTIATORS OF BIOEFFICACY OF ANTI-INFECTIVE DRUGS

CROSS REFERENCE TO RELATED APPLICATION

This application is a divisional of U.S. patent application Ser. No. 11/391,391, filed on Mar. 29, 2006, which claims priority of Indian Patent Application No. 0718/DEL/2005, filed Mar. 31, 2005, the disclosures of which are incorporated by reference herein in their entireties.

FIELD OF THE INVENTION

The present invention relates to the field of chemotherapeutics, particularly use of novel synthetic aromatic amides for potentiating the bioefficacy of specific drugs. The invention particularly relates to the preparation and use of synthetic analogues of aromatic amides, useful in potentiating bioefficacy of anti-infective drugs. The invention more particularly relates to an aromatic amide 4-alkyl-5-(substituted phenyl)-2E,4E-pentadienoic acid amide of structure formula 1a, including its geometrical isomers and di- and tetrahydro derivatives of structure formulae 1b and 1c wherein R represents normal or branched chain C1 to C10 alkyl group, where $R_1$, $R_2$ and $R_3$ independently are the substituents representing hydrogen atom or methoxyl or hydroxyl or halogen or nitro group; where $R_4$ substituent is defined as hydrogen atom or methoxyl group; where $R_2$ and $R_3$ together represent —OCH$_2$O— or —OCH$_2$CH$_2$O— radical or —CH$_2$CH$_2$CH$_2$O— or —CH$_2$CH$_2$C(CH$_3$)$_2$O-radical; where $R_5$ represents hydrogen atom or normal or branched chain C1 to C8 alkyl group or phenyl or benzyl radical and $R_6$ represents hydrogen or C1 to C8 normal or branched chain alkyl group; where NR$_5$R$_6$ together (R$_5$+R$_6$) represent amino acid radical such as alaninyl, leucinyl, phenylalaninyl, tyrosinyl, glycylglycinyl, alanylalaninyl and also represent heterocyclic amine radical such as piperidinyl, pyrrolidinyl, morpholinyl, piperazinyl, N-methylpiperazinyl, pyrrolyl, imidazolyl, oxazolyl or an amino acid such as prolinyl and the like and optionally converting them to their salts by method known in the art of synthesis.

The novel amide when administered in combination with an anti-infective drug, potentiates the bioactivity of the drug thereby requiring lower doses and/or decreased frequency of dosing while maintaining the therapeutic efficacy of standard doses of such drugs.

The synthetic molecules of this invention are all novel as they have not been reported earlier in the literature. These novel molecules possess specific properties of potentiating the bioefficacy of specific drugs particularly they are useful in combination with anti-infective drags which besides reducing their effective dosages are also associated with lesser side effects. The molecules along with the pharmaceutical products/combinations possessing the properties disclosed in the present invention are novel and not known in literature or prior art.

BACKGROUND OF THE INVENTION

A variety of human ailments owe their origin to pathogenic microorganisms, which include bacteria, virus and fungi. The presence of such pathogenic microorganisms lead to septicaemia, serious infections of upper and lower respiratory tract, CNS, meningitis, intra-abdominal including peritoneum, genito-urinary tract, skin, and soft tissue, and variety of other infections like systemic mycosis, candidiasis including infections caused by dermatophytes. During last 100 years, significant progress has been made to combat the diseases caused by such a large family of microbes with innumerable therapeutic agents of diverse chemical and biological nature that have become available as a short and long term cure. Such antimicrobials include aminoglycosides, penicillins, cephalosporins, macrolides, glycopeptides, fluoroquinolones, tetracyclins, first and second line anti-TB drugs, anti-leprosy, anti-virals, polyene, triazole and imidazole anti-fungals, combinations like pyrimidine derivatives and trimethoprim and sulphamethoxizole.

While such agents are effective against pathogenic bacteria and fungi and therefore useful in the treatment of disease conditions associated with the presence of such pathogens, there is increasing evidence that use of such agents has certain limitations and led to clinical concern. There are several such factors responsible for such a concern: (a) certain strains of bacteria and fungi become increasingly resistant to one or more of the known anti-infectives and therefore the usual or standard therapeutic doses lead to less beneficial effect, (b) higher doses that are required to combat the disease cause undesirable side effects and toxicity, and (c) high-cost of treatment and patient-non-compliance. The emergence of drug-resistant pathogenic organisms has also been attributed to uncontrolled antibiotic overuse and under use and even under dosing, irrational frequency of administration. The prolonged and high dose therapy is also a matter of serious concern particularly in pregnant women, geriatrics and children.

While an approach embodying rational use of antibiotics may help slow the problem of microbial drug resistance, new antimicrobial agents must be discovered to combat those strains that are now resistant to most, if not all, currently available antibiotics. As such, there is a continued interest in the identification of novel antimicrobial agents, which can be used to further supplement the medical practitioner's armamentarium against pathogenic microorganisms In another approach, two anti-infectives are combined in such a way that the combination produces synergy i.e. one of the anti-infectives acts as the potentiator of the other anti-infective. The example of such combination is Trimethoprim-Sulfamethoxazole also known as co-trimoxazole or TMP-SMX, which was introduced in 1968 as a broad-spectrum antimicrobial agent. Trimethoprim was specially developed as a potentiator of sulphonamide to act synergistically against bacteria and delay the development of bacterial resistance.

The 1:5 ratio of trimethoprim:sulfamethoxazole achieves an approximate 1:20 ratio of peak serum concentrations which is the optimal synergistic ratio of serum concentrations against most susceptible bacteria (Gutman L T, *Pediatr Infect Dis* 1984; 3:349-57, Olin B R, *Facts and Comparisons, Inc.* 1998; 408b-409d, Cockerill F R, Edson R S, *Mayo Clin Proc* 1991; 66:1260-9).

The combination can also be between one anti-infective agent and another chemical agent which by itself is not anti-infective in nature but when in combination, enhances the effectiveness of the anti-infective drug. The example of such combination is Amoxicillin+Clavulanic acid, more commonly known as Augmentin. Amoxicillin is an antibiotic of the penicillin type. It is effective against different bacteria such as *H. influenzae, N. gonorrhea, E. coli, Pneumococci,*

Streptococci, and certain strains of Staphylococci. Chemically, it is closely related to penicillin and http://www.asiamedicinenet.com/script/main/art.asp?li=AMN&ArticleKey=693 ampicillin. Addition of Clavulanic acid to Amoxicillin in Augmentin enhances the effectiveness of this antibiotic against many other bacteria that are ordinarily resistant to amoxicillin. Clavulanic acid is produced by the fermentation of Streptomyces clavuligerus. It is a β-lactam structurally related to the penicillins and possesses the ability to javascript:defwindow('inactivate') inactivate a wide variety of β-lactamases by javascript:defwindow('blocking') blocking the active sites of these enzymes. Clavulanic javascript:defwindow('acid')acid is particularly active against the clinically important javascri pt:defwindow('plasm id') plasmid mediated β-lactamases frequently responsible for transferred drug resistance to penicillins and cephalosporins.

OBJECTS OF THE INVENTION

The main object of the present invention is to provide the novel aromatic substituted pentadienoic acid amide of general formula 1a including its geometrical isomers, its analogues 1b, 1c and/or their salts thereof.

Another object of the invention is to provide the novel aromatic substituted pentadienoic acid amide which may be useful as potentiators of the bioefficacy of the drugs.

Yet another object of the invention is to provide the process for the preparation of the novel aromatic amides.

Still another objective of the invention is to provide the compounds of formula 1 which are not toxic.

Further object of the invention is to provide the pharmaceutical composition using effective amount of one or more compound of formula 1a including its geometrical isomers, its analogues or and salts thereof as stated above along with the anti-infective drug and optionally along with a carrier or diluent or pharmaceutically acceptable excipient.

Another object of the invention is to provide the pharmaceutical composition which is useful for the treatment of the infections caused by bacteria.

Further object of the invention is to provide the pharmaceutical composition wherein the dose requirement of anti-infectives is reduced.

BRIEF DESCRIPTION OF THE DRAWINGS

FIG.—IA illustrates accumulation of ethidium bromide in wild type and mutant strain, CIP$^r$-1 and effect of compound of formula 1 a where $R_1=R_4=H$; $R_2+R_3=-OCH_2O-$; $R=C_2H_5$; and $R_5+R_6=$piperidinyl (25μg/ml) thereon; and FIG.—IB illustrates efflux of ethidium bromide in wild type and mutant strain, CIP$^r$-1and effect of compound of formula 1 a where $R_1=R_4=H$; $R_2+R_3=-OCH_2O-$; $R=C_2H_5$; and $R_5+R_6=$piperidinyl (25μg/ml) thereon.

DESCRIPTION OF THE INVENTION

Accordingly the present invention provides an aromatic substituted pentadienoic acid amide of general formula 1a-c including its geometrical isomers, its analogues and/or salts thereof

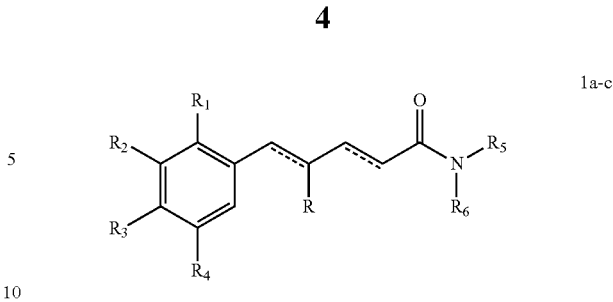

where R represents normal or branched chain C1 to C10 alkyl group and $R_1$, $R_2$ and $R_3$ independently are the substituents representing hydrogen atom or methoxyl or hydroxyl or halogen or nitro group; where $R_4$ substituent is defined as hydrogen atom or methoxyl group; where $R_2$ and $R_3$ together represent $-OCH_2O-$ or $-OCH_2CH_2O-$ radical or $-CH_2CH_2CH_2O-$ or $-CH_2CH_2C(CH_3)_2O-$ radical; where $R_5$ represents hydrogen atom or normal or branched chain C1 to C8 alkyl group or phenyl or benzyl radical and $R_6$ is hydrogen atom or C1 to C8 normal or branched chain alkyl group; where $NR_5R_6$ together $(R_5+R_6)$ represent amino acid radical such as alaninyl, leucinyl, phenylalaninyl, tyrosinyl, glycylglycinyl, alanylalaninyl and also represent heterocyclic amine radical such as piperidinyl, pyrrolidinyl, morpholinyl, piperazinyl, N-methylpiperazinyl, pyrrolyl, imidazolyl, oxazolyl or an amino acid radical such as prolinyl; dotted lines indicate the presence of double and single bonds.

The structural formula of compound of general formula 1a as stated above

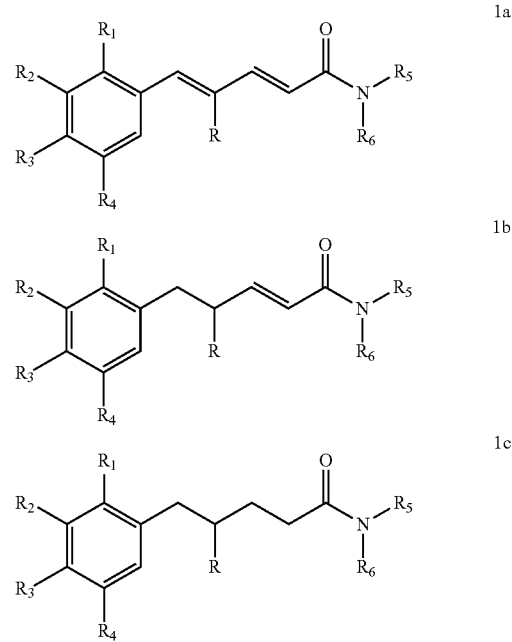

wherein R represents normal or branched chain C1 to C10 alkyl group and $R_1$, $R_2$ and $R_3$ independently are the substituents representing hydrogen atom or methoxyl or hydroxyl or halogen or nitro group; where $R_4$ substituent is defined as hydrogen atom or methoxyl group; where $R_2$ and $R_3$ together represent $-OCH_2O-$ or $-OCH_2CH_2O-$ radical or $-CH_2CH_2CH_2O-$ or $-CH_2CH_2C(CH_3)_2O-$ radical; where $R_5$ represents hydrogen atom or normal or branched chain C1 to C8 alkyl group or phenyl or benzyl radical and $R_6$ is hydrogen atom or C1 to C8 normal or branched chain alkyl group; where $NR_5R_6$ together $(R_5+R_6)$ represent amino acid radical such as alaninyl, leucinyl, phenylalaninyl, tyrosinyl, glycylglycinyl, alanylalaninyl and also represent heterocyclic amine radical such as piperidinyl, pyrrolidinyl, morpholinyl, piperazinyl, N-methylpiperazinyl, pyrrolyl, imidazolyl, oxazolyl or an amino acid radical such as prolinyl.

In an embodiment of the invention wherein the salt is pharmaceutically acceptable selected from hydrochloride, acetate, succinate, maleate.

Accordingly the present invention provides a process for the preparation of aromatic substituted pentadienoic acid amides of general formula 1a-c wherein the method of preparation of the said compounds comprising the steps of;

(i) reacting aromatic aldehyde of formula 2 wherein $R_1$, $R_2$ and $R_3$ independently are the substituents representing hydrogen atom or methoxyl or hydroxyl or halogen or nitro group; where $R_4$ substituent is defined as hydrogen atom or methoxyl group; wherein $R_2$ and $R_3$ together represent —$OCH_2O$— or —$OCH_2CH_2O$— radical or —$CH_2CH_2CH_2O$— or —$CH_2CH_2C(CH_3)_2O$— radical, with an alkyl magnesium halide preferably ethyl magnesium halide or higher homologues with constant stirring at ambient temperature in an anhydrous ether or tetrahydrofuran as solvent to produce corresponding 1-(substituted phenyl) alkanol of formula 3 wherein $R_1$, $R_2$ and $R_3$ independently are the substituents representing hydrogen atom or methoxyl or hydroxyl or halogen or nitro group; where $R_4$ substituent is defined as hydrogen atom or methoxyl group; wherein $R_2$ and $R_3$ together represent —$OCH_2O$— or —$OCH_2CH_2O$— radical or —$CH_2CH_2CH_2O$— or —$CH_2CH_2C(CH_3)_2O$— radical, R represents normal or branched chain C1 to C10 alkyl group;

(ii) treating the compound of formula 3 with dimethylformamide and phosphorus oxychloride mixture at 0-10° C. for 20-80 hours to produce 2-alkyl-(substitutedphenyl)-2E-propenaldehyde of formula 4 wherein R represents normal or branched chain C1 to C10 alkyl group and $R_1$ to $R_4$ are the substituents/radicals as described above;

(iii) reacting the compound of formula 4 with a Wittig reagent prepared from triphenyl phosphine and bromoalkyl acetate, in presence of a base at temperature in the range of 5-80° C. for a period in the range of 1-120 hours, followed by isolation of the crude pentadienoic ester by conventional method and hydrolysis in alkaline solution to produce 2-alkyl-(substitutedphenyl)-2E-4E-pentadienoic acid or its geometrical isomer of formula 6 wherein R, $R_1$ to $R_4$ are the substituents/radicals as described above;

(iv) converting pentadienoic acid of formula 6 to corresponding acid chloride using thionyl chloride and reacting the acid chloride with nitrogenous compounds as defined in claim 1 in an inert organic solvent at temperature in the range of 0-50° C., isolating the compound of formula 1a where R represents normal or branched chain C1 to C10 alkyl group and $R_1$, $R_2$ and $R_3$ independently are the substituents representing hydrogen atom or methoxyl or hydroxyl or halogen or nitro group; where $R_4$ substituent is defined as hydrogen atom or methoxyl group; where $R_2$ and $R_3$ together represent —$OCH_2O$— or —$OCH_2CH_2O$— radical or —$CH_2CH_2CH_2O$— or —$CH_2CH_2C(CH_3)_2O$— radical; wherein $R_5$ represents hydrogen atom or normal or branched chain C1 to C8 alkyl group or phenyl or benzyl radical and $R_6$ represents hydrogen or C1 to C8 normal or branched chain alkyl group; where $NR_5R_6$ together $(R_5+R_6)$ represent amino acid radical such as alaninyl, leucinyl, phenylalaninyl, tyrosinyl, glycylglycinyl, alanylalaninyl and also represent heterocyclic amine radical such as piperidinyl, pyrrolidinyl, morpholinyl, piperazinyl, N-methylpiperazinyl, pyrrolyl, imidazolyl, oxazolyl or an amino acid such as prolinyl and optionally converting them to their salts by known method by reacting with an acidic compound such as hydrochloric acid, acetic acid, tartaric acid etc.;

(v) preparing the compound of formula 1c by converting the 2-alkyl-(substituted phenyl)-2E-4E-pentadienoic acid of formula 6 to corresponding tetrahydro derivative 8 by hydrogenation in presence of Pd/charcoal in polar or medium polar solvent at ambient temperature and 1-3 atmospheric pressure wherein R and $R_1$ to $R_4$ are the substituents/radicals as described above, the compound of formula 8 is then converted to corresponding amides of formula 1c by the method described as above for compound of formula 1a where R and $R_1$ to $R_6$ are the substituents/radicals as described, alternatively compound of formula 1c may also be prepared by hydrogenation from compound of formula 1a directly with hydrogen in presence of Pd/C in polar or medium polar solvent at ambient temperature and 1-3 atmospheric pressure;

(vi) preparing the compound of formula 1b by subjecting the intermediate 2-alkyl-(substitutedphenyl)-2E-propenaldehyde of formula 4 where R and $R_1$ to $R_4$ are the substituents/radicals as described above, to hydrogenation in presence of Pd/C in polar or medium polar solvent at ambient temperature and 1-3 atmospheric pressure to furnish corresponding dihydro derivative of formula 5 wherein R and $R_1$ to $R_4$ are the substituents/radicals as described above, which was then subjected to Wittig reaction followed by saponification as described in the preparation of compound of formula 6 wherein $R_1$ to $R_4$ are the substituents/radicals as described above to furnish compound of formula 7 where $R_1$ to $R_4$ are the substituents/radicals as described above which is subsequently converted to amides of formula 1b by the same method as described for the preparation of compound of formula 1a wherein R and $R_1$ to $R_6$ are the substituents/radicals as described above.

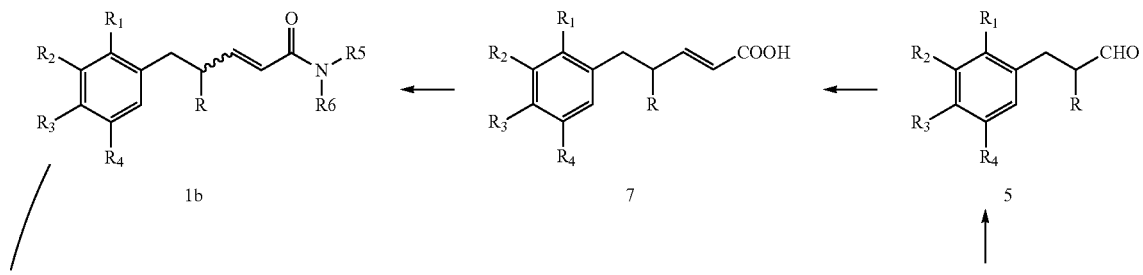

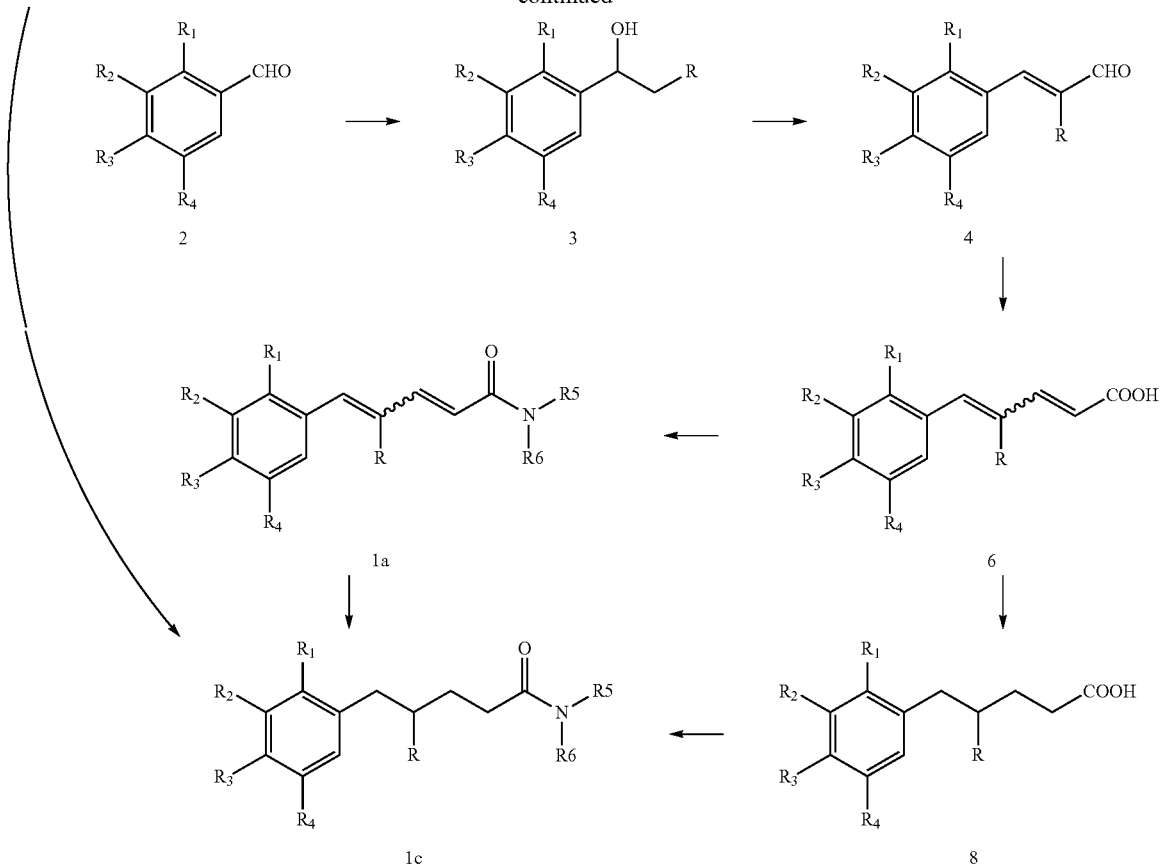

Embodiments Of The Invention

In an embodiment of the invention wherein the use of compound of formula 1a-c including its geometrical isomers as potentiator of bioefficacy of anti-infective drugs.

In another embodiment of the invention wherein the process further comprises converting the compound of formula 1a-c into a salt.

Accordingly, the present invention provides a pharmaceutical composition comprising an effective amount of one or more compound of formula 1a-c including its geometrical isomers, its analogues or and salts thereof as stated above along with the anti-infective drug and optionally along with a carrier or diluent or pharmaceutically acceptable exciepient.

In an embodiment of the invention the amount of compound of formula 1 may vary from 0.1 to 50% by weight of the composition with respect to the drug.

In another embodiment of the invention wherein the composition is useful as anti-microbial agent.

In yet another embodiment of the invention wherein the MIC value of composition is reduced more than 8 times of the anti-infective drugs when used alone.

In an another embodiment of the invention wherein the ED50 of anti-infective drug reduced to about one half when used in combination with the compound of formula 1a-c.

In still another embodiment of the invention wherein the dose of anti-infective drugs is reduced about one fourth when used in combination with compounds of formula 1a-c.

In further embodiment of the invention wherein the anti-infectives are selected from groups comprising of penicillins (including semi-synthetic), cephalosporins, aminoglycosides, glycopeptides, fluoroquinolones, macrolides, tetracyclines other antibiotic groups such as mupirocin and framycetin, first and second line anti-TB drugs, anti-leprosy drugs, oxazolidinones In an embodiment of the invention wherein the composition is effective against microorganisms selected from gram positive bacteria such as *Staphylococcus species* and *Bacillus* species.

In still another embodiment of the invention wherein the composition is effective against microorganisms selected from gram negative bacteria such as *Pseudomonas* species, *E. coli* and *Salmonella* species.

In one more embodiment of the invention wherein the composition is effective against microorganisms such as *Mycobacterium* species.

In another embodiment of the invention wherein composition is effective against growth of microorganisms otherwise resistant (such as MRSA) to some anti-infectives are also inhibited.

In a further embodiment of the invention wherein composition is effective when tested for curing of mice, guinea pig or rabbit models infected with microorganisms from the gram positive group of bacteria such as *Staphylococcus species* and *Bacillus* species.

In an embodiment of the invention wherein composition is effective when tested for curing of mice, guinea pig or rabbit models infected with microorganisms from the gram negative group of bacteria such as *Pseudomonas* species, *E. coli* and *Salmonella* species.

In an embodiment of the invention wherein composition is effective when tested for curing of mice, guinea pig or rabbit models infected with microorganisms from the bacteria such microorganisms such as *Mycobacterium* species.

In an embodiment of the invention wherein the said composition along with excipient or pharmaceutical vehicle such as lactose, corn starch, polyethylene glycols and the like may be administered through oral route.

In an embodiment of the invention wherein the said composition along with excipient or pharmaceutical vehicle such as castor oil, olive oil and the like may be administered through systemic route.

In an embodiment of the invention wherein the said composition along with excipient or pharmaceutical vehicle such as polyethylene glycols, bees wax, paraffin wax, emulsifying agents and the like may be applied topically.

A method for inhibiting a bacterial cell that employs an efflux pump resistance mechanism, comprising contacting the cell with a pharmaceutical composition comprising of an antibacterial agent and a compound of formula 1a-c and optionally an excipient or pharmaceutical vehicle.

In an embodiment of the present invention wherein the bacterial cell is selected from gram positive bacteria such as *Staphylococcus species* and *Bacillus* species.

In one more embodiment of the invention wherein the bacterial cell is selected from gram negative bacteria such as *Pseudomonas species, E. coli* and *Salmonella* species.

In a further embodiment of the invention wherein the bacterial cell is selected from mycobacterial species.

A method of treating infections comprising administrating to a subject in need of such treatment a therapeutically effective amount of compound of formula 1a-c including its geometrical isomers, its analogues or and salts thereof as claimed in claim 1 along with the anti-infective drug and optionally along with a carrier or diluent or pharmaceutically acceptable exciepient.

In one of the embodiment of the invention wherein the infection caused by a bacteria that employs an efflux pump resistance as one of the ways of resistance, comprising administering to a patient in need thereof a therapeutically effective amount of an antibacterial agent and a compound of formula 1a-c.

The present invention deals with such combinations comprising 4-alkyl-5-(substituted phenyl)-2E,4E-pentadienoic acid amide including its geometrical isomers and di- and tetrahydro derivatives of formulae 1a, 1b and 1c wherein R, $R_1$-$R_6$ are as described above and as a representative example of formula 1 where R=$C_2H_5$, $R_1$=$H_4$=H, $R_2$+$R_3$=—OCH$_2$O— and $R_5$+$R_6$=piperidinyl, displayed the properties of potentiation/synergism in vitro screening when combined with various anti-infective agents using bacteria, viruses and yeast. These combinations were also efficacious when tested in in vivo using mice and guinea pig models infected with microorganisms (table-7). Another representative example may be 4-alkyl-5-(substituted phenyl)pentanoic acid amide where R=$C_2H_5$, $R_1$=$R_4$=H, $R_2$+$R_3$=—OCH$_2$O— and $R_5$+$R_6$=isobutyl aminyl in formula 1c that has displayed the properties of potentiation/synergism when combined with various anti-infective agents in vitro using bacteria, viruses and yeast and in vivo using mice and guinea pig infection models(table-7).

The present invention is aimed to circumvent such problems and use of the products of the present invention offer a low dose regimen that produces enhanced therapeutic action comparable to that of standard dose of a drug alone.

The compounds of the present invention are neither reported in the chemical literature nor have been used for the purpose of potentiating the bioefficacy of the drugs particularly anti-infective drugs such as described in the present invention. The syntheses of the novel compounds have been accomplished through the combination of various chemical steps known in the art of synthesis though not for the purpose of synthesising the novel compound of formula 1a-c as described above.

The aromatic amide of formula 1a i.e. 4-alkyl-5-(substituted phenyl)-2E,4E-pentadienoic acid amide, its geometrical isomer 4-alkyl-5-(substituted phenyl)-2E,4Z-pentadienoic acid amide of formula 1 and its di and tetrahydro derivatives of the formula 1b and 1c wherein R and $R_1$-$R_6$ are described as above, were synthesised from the corresponding aromatic aldehydes. The substituted aromatic aldehyde was first reacted with alkyl magnesium halide with constant stirring at ambient temperature in an anhydrous ether solvent such as diethyl ether, tetrahydrofuran and the like to produce corresponding 1-(phenyl) alkanol(propanol or higher homologs) which is treated with dimethylformamide and phosphorus oxychloride mixture at 0-10° C. for 20-80 hrs, contents neutralised with dilute alkali solution to produce 2-alkyl-3-(substituted phenyl)-2E-propenaldehyde. The 2-alkyl-3-(substituted phenyl)-2E-propenaldehyde was condensed with an ylide (Wittig reagent) prepared from triphenylphosphine, and methyl/ethyl bromoacetate in equimolar mixture in presence of a strong base such as sodium hydride, sodium methoxide and the like at temperature 5-80° C. for 1 to 24 hrs in an ethereal medium such as diethyl ether, dimethoxyethane and the like or benzene/toluene or dimethylformamide to yield corresponding ethyl 4-substituted phenyl-2E,4E-pentadienoate and/or its geometrical isomer 4-alkyl-5-(substituted phenyl)-2E,4Z-pentadienoate which were hydrolysed with a strong alkali solution using sodium hydroxide or potassium hydroxide followed by acidification to furnish 4-substituted phenyl-2E,4E-pentadienoic acid and/or 4-substituted phenyl-2E,4Z-pentadienoic acid. A solution of aryl alkenoic acid as prepared above in an inert organic solvent such as benzene, dichloromethane is treated with thionyl chloride and excess of solvent removed. The acyl chloride intermediate thus obtained without purification is condensed with acyclic or cyclic or heterocyclic amine or an amino acid in inert organic solvent such as dichloromethane, benzene, diethyl ether and the like in the temperature range of 0° to 50° C., and after the purification by crystallisation or column chromatography to produce aromatic amide of formula 1a. The compound of formula 1b is prepared by hydrogenation of intermediate 2-alkyl-3-(substitutedphenyl)-2E-propenaldehyde in presence of Pd/charcoal and hydrogen gas in a polar solvent such as methanol/ethyl acetate to give 2-alkyl-3-(substitutedphenyl)propanal. The propanal thus obtained is subjected to Wittig reaction, alkaline hydrolysis and amide formation with acyclic or cyclic or heterocyclic amine as described for the formation of compound of formula 1a. For the preparation of compound of formula 1e, the dihydroacid of formula 7 is converted to its tetrahydro derivative by hydrogenation in presence of Pd/charcoal in polar solvent such as methanol or ethnaol at ambient temperature and at 1-3 atmospheric pressure to obtain corresponding tetrahydro derivative which is converted to corresponding amides of formula 1e by the method described as above for the preparation of compound of formula 1a. Alternatively 1e may also be prepared by hydrogenation of compound of formula 1a as such by the method as described above.

Bio Efficacy

New antibiotics are continued to be discovered at a rate of >500/year, but these almost invariably belong to previously identified classes of compounds, making it likely that pathogens will be able to rapidly build up resistance to these "new"

drugs. The increasing threat of drug-resistant pathogens is causing a renewed interest in the discovery of novel antibiotics.

Present invention is focused on 'potentiators' involved wherein such agents, which by themselves are not therapeutic entities but when combined with an active drug, lead to the potentiation of the pharmacologic effect of the drug. Such formulations/combinations have been found to increase the bioefficacy of a number of drugs even when reduced doses of drugs are present in such formulations. Evidence have been obtained for such classes of drugs which are (a) poorly bioavailable and/or efficacious, (b) require prolonged therapy, and (c) are highly toxic and expensive. For example, Patent nos. IP 172690, IP 176433 and U.S. Pat. No. 5,744,161 disclose such art. These compounds are not only capable of increasing bioavailability of a wide variety of therapeutic agents but are also capable of enhancing bioefficacy through a variety of mechanisms. As a result newer understanding has emerged about the factors involved in decreased cellular concentrations of drugs at which they fail to attain therapeutic levels and the strategies that make it possible to enhance the bioefficacy of these active drugs even at lower concentrations compared to standard high dosing. Some of these factors are:

(a) Increasing the penetration or entry of the active drug into the pathogen even where they become persistors, besides inhibiting the capability of pathogens and abnormal tissues to reject the drug. This would eventually ensure the enhanced killing of the pathogenic microorganisms, which are otherwise inaccessible to the active drug.
(b) Chemoresistance is a major problem in drug therapy. The mechanisms underlying the clinical phenomena of de novo and acquired drug resistance may arise from alterations at any step in the cell-killing pathway. These include drug transport, drug metabolism, drug targets, cellular repair mechanisms and the ability of cells to recognize a harmful toxin or pathogen. A common mechanism of reduced cellular drug accumulation is the increased expression Multi Drug Resistance pumps (MDRs). The present invention also proves that the compounds described here inhibit the bacterial efflux, as a result of which there is more of accumulation and decreased efflux of ethidium bromide. When compared with piperine (a known p-glycoprotein inhibitor and bacterial efflux pump inhibitor) these compounds were more potent inhibitors of bacterial efflux pumps.
(c) Immunological intervention through NO production, CMI and/or humoral immune potentiation with favourable influence on the Th 1/Th 2 balance.
(d) Sensitization of specific receptors like proteins, DNA, RNA etc thus potentiating and prolonging the effect leading to enhanced antibiotic activity against pathogens, and disorders. Adequate experimental evidences have been gained in respect of several of these mechanisms. For example, piperine has been shown to intercalate deeply into the phospholipids of the cell membrane, (Ray et al, *Ind. J Biochem. Biophys* 1999; 36: 248-251) modulating the membrane fluidity, which may alter the activity of membrane bound transporter proteins. The overall permeability changes may affect (i) specific ion transporter channels, and (ii) also lead to bulk movement of lipophilic solutes along the paracellular pathway. Such membrane changes have also been evidenced in the action of several polyene antibiotics (Milhaud J et al, *Biochimica et Biophysica Acta,* 1988; 943:315-325).
(e) Potentiating the mechanism of action of drugs and thus increasing their efficacy at lower doses e.g. inhibition of RNA polymerase transcription leading to potentiation of the effect of rifampicin at less than half the standard dose.

The products of the present invention are novel mechanism based pharmaceutical entities acting through synergism and/or additive effect so that drugs contained in the formulation are more bioefficaceous as a result of one or more of the mechanism as revealed above and thereby increasing the sensitivity of the target cell to an anti-infective.

Description Of Preferred Embodiments

The 'drug' in the present invention refers to a chemical entity capable of affecting organism's patho-physiology and used for the treatment or prevention of disease. Drugs include a number of classes of compounds, but not limited to aminoglycoside, penicillins, cephalosporins and other β-lactam agents, macrolides, glycopeptides, fluoroquinolones, tetracyclines, first and second line anti-TB drugs, anti-leprosy, antivirals, polyene, triazole, and imidazoles and combinations like pyrimidines, sulphamethoxazole. Drugs may be a prodrug, activated or metabolised form, consisting of charged, uncharged, hydrophilic, hydrophobic or zwitter-ion species which make their entry by simple diffusion, carrier mediated transport dependent and not dependent on energy requirements, through ion and/or voltage gated channels.

The 'potentiator' refers to aromatic amides of the formulae 1a-c selected from the following set of compounds prepared by the method described in the examples 5-(3,4-methylenedioxyphenyl)-4-methyl-2E,4E-pentadienoic acid piperidide
5-(3,4-methylenedioxyphenyl)-4-methyl-2E,4E-pentadienoic acid pyrrolidide
5-(3,4-methylenedioxyphenyl)-4-methyl-2E,4E-pentadienoic acid-N,N-diethylamide
5-(3,4-methylenedioxyphenyl)-4-methyl-2E,4E-pentadienoic acid-n-butylamide
5-(3,4-methylenedioxyphenyl)-4-methyl-2E,4E-pentadienoic acid isobutylamide
5-(3,4-methylenedioxyphenyl)-4-methyl-2E,4E-pentadienoic acid morpholide
5-(3,4-methylenedioxyphenyl)-4-methyl-2E,4E-pentadienoic acid-N-methylpiperazide
5-(3,4-methylenedioxyphenyl)-4-methyl-2E,4E-pentadienoic acid-4-hydroxypiperidide
5-(3,4-methylenedioxyphenyl)-4-methyl-2E,4E-pentadienoic acid-1-(4-bromophenyl)ethylamide
5-(3,4-methylenedioxyphenyl)-4-methyl-2E,4E-pentadienoic acid 2-(hydroxymethyl)propylamide
5-(3,4-methylenedioxyphenyl)-4-methyl-2E,4E-pentadienoic acid n-octylamide
5-(3,4-methylenedioxyphenyl)-4-ethyl-2E,4E-pentadienoic acid piperidide
5-(3,4-methylenedioxyphenyl)-4-ethyl-2E,4E-pentadienoic acid pyrrolidide
5-(3,4-methylenedioxyphenyl)-4-ethyl-2E,4E-pentadienoic acid-N,N-diethylamide
5-(3,4-methylenedioxyphenyl)-4-ethyl-2E,4E-pentadienoic acid isobutylamide
5-(3,4-methylenedioxyphenyl)-4-ethyl-2E,4E-pentadienoic acid-n-butylamide
5-(3,4-methylenedioxyphenyl)-4-ethyl-2E,4E-pentadienoic acid morpholide
5-(3,4-methylenedioxyphenyl)-4-ethyl-2E,4E-pentadienoic acid-N-methylpiperazide
5-(3,4-methylenedioxyphenyl)-4-ethyl-2E,4E-pentadienoic acid-4-hydroxypiperidide
5-(3,4-methylenedioxyphenyl)-4-ethyl-2E,4E-pentadienoic acid imidazolide
5-(3,4-methylenedioxy-5-nitrophenyl)-4-ethyl-2E,4E-pentadienoic acid piperidide 5-(3,4-methylenedioxyphenyl)-4-ethyl-2E,4E-pentadienoicacid-α-carbomethoxy methylamide
5-(3,4-methylenedioxyphenyl)-4-ethyl-2E,4E-pentadienoic acid-(2-pyridyl)amide
5-(3,4-methylenedioxyphenyl)-4-ethyl-2Z,4E-pentadienoic acid piperidide
5-(3,4-methylenedioxyphenyl)-4-ethyl-2E,4Z-pentadienoic acid piperidide
5-(3,4-methylenedioxyphenyl)-4-ethyl-2E-pentenoic acid piperidide
5-(3,4-methylenedioxyphenyl)-4-ethyl-pentanoic acid piperidide
5-(3,4-methylenedioxyphenyl)-4-methyl-pentanoic acid piperidide
5-(3,4-methylenedioxyphenyl)-4-n-propyl-2E,4E-pentadienoic acid piperidide
5-(3,4-methylenedioxyphenyl)-4-n-butyl-2E,4E-pentadienoic acid piperidide
5-(3,4-methylenedioxyphenyl)-4-n-butyl-2E,4E-pentadienoic acid-4-hydroxy piperidide
5-(3,4-methylenedioxyphenyl)-4-n-butyl-2E,4E-pentadienoic acid-4-N-methyl piperazide
5-(4-methoxyphenyl)-4-methyl-2E,4E-pentadienoic acid piperidide
5-(4-methoxyphenyl)-4-ethyl-2E,4E-pentadienoic acid piperidide
5-(4-methoxyphenyl)-4-propyl-2E,4E-pentadienoic acid piperidide
5-(4-methoxyphenyl)-4-n-butyl-2E,4E-pentadienoic acid piperidide
5-(4-methoxyphenyl)-4-n-hexyl-2E,4E-pentadienoic acid piperidide
5-(4-methoxyphenyl)-4-n-propyl-2E,4E-pentadienoic acid-N-methylpiperazide
5-(3,4-dimethoxyphenyl)-4-ethyl-2E,4E-pentadienoic acid piperidide
5-(3,4-ethylenedioxyphenyl)-4-ethyl-2E,4E-pentadienoic acid piperidide
5-(3,4-dimethoxyphenyl)-4-ethyl-2E,4E-pentadienoic acid pyrrolidide
5-(2,2-dimethyl-2H-benzopyran-6-yl)-4-ethyl-2E,4E-pentadienoic acid piperidide
5-(2,2-dimethyl-2H-benzopyran-6-yl)-4-ethyl-2E,4E-pentadienoic acid pyrrolidide The ratio of a potentiator to drugs may vary from 0.1 to 50% to obtain desired reduction in MIC values for anti-infectives. The ratios of the drug and the potentiator and/or in composite potentiators are governed by amounts sufficient to produce enhanced therapeutic efficacy as measured by MIC of the formulation being lesser than the drug alone. A pharmaceutical carrier is generally an inert bulk agent added to make the ingredients achieve superior admixing and can be solid or liquid. The inert parts of standard pharmaceutical compositions used in this process are also part of the present invention.

Study Design
The Checkerboard Method:
This is the most frequently used method to access the antimicrobial combinations in vitro. The term "checkerboard" refers to the pattern (of tubes or microtiter plate wells) formed by multiple dilutions of two drugs being tested (Eliopoulos G M, Moellering R C. Antimicrobial Combinations, in: Antibiotics in Laboratory Medicine: USA: Williams & Wilkins). In the present study the checkerboard consisted of columns in which each tube (or well) contains the same amount of the standard drug (antibacterial/antifungal/anti-TB/antirviral) being diluted along the x-axis and rows in which tube (or well) contains the same amount of the potentiator being diluted on the y-axis. As a result each square in the checkerboard (which represents one tube/well or plate) contained a unique combination of the standard drug and potentiator. The concentration range of standard drug in the present study was 64 μg/ml to 0.03 μg/ml, whereas the potentiator was tested in the range of 500 μg/ml to 0.2 μg/ml.

This checkerboard technique can be performed with liquid or semisolid (agar) media.

Agar Method:
In this method the agar (Mueller Hinton agar, Middlebrook 7H10 agar) was autoclaved and allowed to cool to 55° C. to 50° C. The combination of the standard drug and the potentiator was added to the agar. Serial two fold dilutions of each of standard drug and the potentiator were prepared in appropriate solvents. In order to maintain the desired concentrations of both agar and drugs, and to rule out the effect of solvent, the volume of solvent (containing standard drug or potentiator) added to agar was kept small (i.e ≤5% of the total volume). After the agar plates have been poured and allowed to dry, the bacteria to be tested were applied to the surface of agar with a replicating device designed to deliver a standard inoculum (approx $10^4$ cfu|spot). The plates were incubated at 37° C. for 24 hrs (3 weeks in case of *Mycobacterium tuberculosis*)

Broth Method:
The above-mentioned checkerboard was also performed with liquid media in a microtiter plate format. This method was used to study the combination of antibacterial/antifungal/antiviral drugs with potentiator.

Toxicity evaluation of 4-ethyl-5-(3,4-methylenedioxyphenyl)-2E,4E-pentadienoic acid piperidine amide of formula 1a In acute toxicity studies an $LD_{50}$ (oral) was found to be >3.0 gm/kg in mice. In subacute studies the effect of 4-ethyl-5-(3,4-methylenedioxyphenyl)-2E,4E-pentadienoic acid piperidine amide of formula 1 at 20, 40 and 100 mg/kg was investigated for 28 days. Parameters monitored were: Food/water consumption, body weight, organ weight, haematological and clinical chemistry profile. No adverse effects were observed. Safety pharmacology studies (CNS, CVS and GIT profile) did not reveal any abnormality.

The following examples are intended to demonstrate some of the preferred embodiments but in no way be construed so as to limit the scope of the invention. Any person skilled in the art can design more formulations, which may be considered as part of the present invention.

Example 1

Syntheses of 4-methyl-5-(3,4-methylenedioxyphenyl)-2E,4E-pentadienoic acid piperidine amide of formula 1a where $R_1=R_4=H$; $R_2+R_3=$ —OCH$_2$O—, R=CH$_3$ and $R_5$-$R_6$=piperidinyl (i) Preparation of 1-(3,4-methylenedioxyphenyl) propan-1-ol

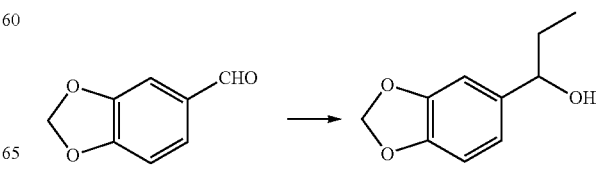

A solution of 3,4-methylenedioxybenzaldehyde (4.5 g, 30 mmol) of formula 2 prepared in dry diethyl ether is slowly added to an ethereal solution of Grignard reagent prepared from magnesium metal (0.84 g, 35 mmol) and iodoethane (3.0 ml, 40 mmol) and the contents stirred for 1 hour at room temperature. After the completion of the reaction, the mixture is processed by adding saturated aqueous solution of ammonium chloride (10 ml) followed by dilution with water (100 ml), separating the organic layer and extracting the aqueous layer with solvent ether (2×100 ml). The combined organic layer washed with water (2×20 ml) dried over anhydrous sodium sulfate and concentrated in vacuo to yield 1-(3,4-methylenedioxyphenyl) propan-1-ol, a semisolid of formula 3(5.3 g, 97.5%).

(ii) Preparation of 2-methyl-3-(3,4-methylenedioxyphenyl)-2E-propenal

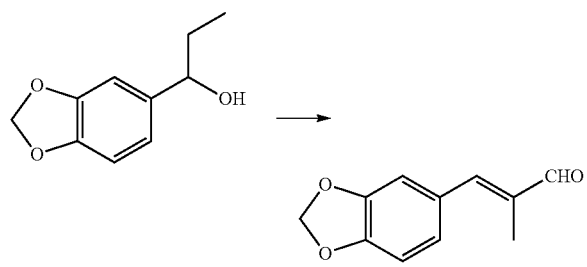

A solution of 1-(3,4-methylenedioxyphenyl) propan-1-ol of (4.8 g, 27 mmol) of formula 3 in dimethylformamide (10 ml) is slowly added to phosphorus oxychloride (8 ml) in DMF (12 ml) with stirring while maintaining the temperature at 0° C. The reaction mixture is stirred for 2 hour then allowed to attain room temperature followed by heating on an oil bath for 36 hour at 40° C. After the completion of the reaction as monitored by TLC, contents of the reaction mixture are poured into ice-cold water (500 ml), neutralised with dilute alkali solution and saturated by adding sodium chloride. The aqueous portion is extracted with ethyl acetate (3×100 ml), organic layer washed with water, dried over anhydrous sodium sulphate and stripped off the solvent under reduced pressure to furnish crude product (4.8 g). It was purified by column chromatography over silica gel to yield a semi-solid 2-methyl-3-(3,4-methylenedioxyphenyl)-2E-propenal of formula 4 (4.1 g, 80%).

(iii) Preparation of 4-methyl-5-(3,4-methylenedioxy phenyl)-2E,4E-pentadienoic acid

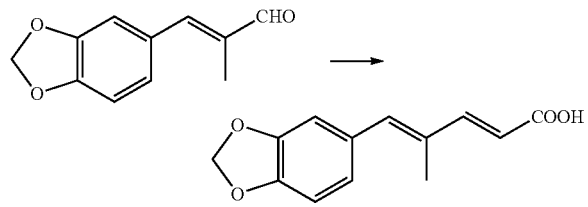

A mixture of triphenylphosphine (4.7 g, 18 mmol) and ethyl bromoacetate (20 ml, 18 mmol) in anhydrous dimethoxyethane is refluxed for 2 hour, concentrated and to the intermediate thus formed, sodium hydride (0.5 g) in dry ether at 0-5° C. is added with stirring to obtain intermediate ylide. An ethereal solution of 2-methyl-3-(3,4-methylenedioxyphenyl)-2E-propenal (2.5 g, 13 mmol) of formula 4 prepared in step (ii) above is added to ylide solution and after 24 hours an additional amount of sodium hydride (0.5 g) is added. The reaction mixture is continuously stirred for 72 hour at 40° C. On cooling, the contents are diluted with ethyl acetate (100 ml) to quench unused sodium hydride, then diluted with water (200 ml), organic layer separated and the aqueous layer extracted with ethyl acetate (2×100 ml). The combined organic layer washed with water (2×30 ml) and concentrated under reduced pressure. The crude 4-methyl-5-(3,4-methylenedioxyphenyl)-2E,4E-pentadienoate obtained above is hydrolysed directly without purification in 10% methanolic potassium hydroxide solution on a water bath for 3 hour, the contents concentrated and diluted with water (120 ml) and extracted with ethyl acetate (2×10 ml) and the aqueous layer acidified with 2N hydrochloric acid solution. The resulting precipitate is filtered, washed with water and air dried to furnish crude acid (2.40 g, 80%). Crystallisation of the crude acid from ethyl acetate:benzene (19:1) furnished pure 4-methyl-5-(3,4-methylenedioxyphenyl)-2E,4E-pentadienoic acid of formula 6.

(iv) Preparation of 4-methyl-5-(3,4-methylenedioxyphenyl)-2E,4E-pentadienoic acid piperidine amide of formula 1a where $R_1=R_4=H$; $R_2+R_3=$ $-OCH_2O-$, $R=CH_3$ and $R_5+R_6=$piperidinyl

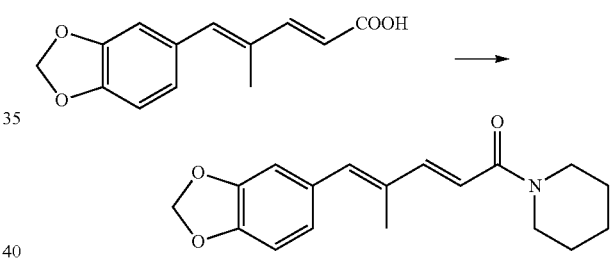

Freshly distilled thionyl chloride (0.5 ml) is added to a dichloromethane solution of 4-methyl-5-(3,4-methylenedioxyphenyl)-2E,4E-pentadienoic acid (1.4 g, 6 mmol) of formula 6 obtained in step (ii) the mixture is refluxed on a water bath for 1 hour. Solvent is removed from the acid chloride under reduced pressure along with excess of thionyl chloride. A solution of piperidine (0.6 ml, 7 mmol) in dichloromethane is slowly added to the acid chloride prepared above and mixture stirred for 1 hour. After completion of the reaction, the organic layer is made free of excess of piperidine using dilute hydrochloric acid solution. The organic layer is washed with water, dried and concentrated under vacuum to furnish crude product (1.7 g, 94%), purified by crystallisation from ethyl acetate:hexane (9:1) to yield 4-methyl-5-(3,4-methylenedioxyphenyl)-2E,4E-pentadienoic acid piperidine amide of formula 1a (1.62 g, 90%).

Example 2

Preparation of 4-methyl-5-(3,4-methylenedioxyphenyl)pentanoic acid piperidide of formula 1c where $R_1=R_4=H$; $R_2+R_3=-OCH_2O-$, $R=CH_3$ and $R_5+R_6=$piperidinyl To an ethanolic solution (30 ml) of 4-methyl-5-(3,4-methylenedioxyphenyl)-2E,4E-pentadienoic acid piperidine amide (0.60 g, 2.0 mmol) formula 1a prepared by the method described in example 1 was added Pd/C (10%, 100 mg) and the contents stirred at 40 psi in hydrogenation bottle and after the completion of the reaction (14 hrs.), the reaction mixture was filtered, washed with ethanol(3×10 ml) and concentrated to obtain title compound of formula is in almost quantitative yield.

Example 3

Synthesis of 4-ethyl-5-(4-methoxyphenyl)-2E,4E-pentadienoic acid piperidide of formula 1a where $R_1=R_2=R_4=H$; $R_3=$—$OCH_3$, $R=$—$CH_2CH_3$ and $R_5+R_6=$4-hydroxypiperidyl The title compound was prepared from 4-methoxybenzaldehyde (5.2 g, 38 mmol) by subjecting it to Grignard's reaction with 1-n-bromopropane by the method described in example 1(i) to give 1-(4-methoxyphenyl)-n-butanol of formula 3 (6.7 g, yield 98%). The secondary alcohol (5.55 g, 30 mmol) was subjected to Vilsmeier reaction with dimethyl formamide-phosphorous oxychloride as described in example 1 (ii) to furnish 2-formyl-1-(4-methoxyphenyl)-1-butene of formula 4 (4.0 g, 70%). The resulting aldehyde (3.8 g, 20 mmol) was subjected to Wittig reaction as described in example 1 (iii) followed by saponification to produce 5-(4-methoxyphenyl)-4-ethyl-2E,4E-pentadienoic acid of formula 6(3.0 g, 65%). The pentadienoic acid (1.0 g, 4.3 mmol) after acid chloride formation with thionyl chloride, and reaction with 4-hydroxypiperidine was purified by column chromatography on silica gel to give 5-(4-methoxyphenyl)-4-ethyl-2E,4E-pentadienoic acid piperidide of formula 1a (0.84 g, 60%).

Example 4

Syntheses of 4-n-propyl-5-(3,4-methylenedioxyphenyl)-2E,4E-pentadienoic acid piperidine amide of formula 1a where $R_1=R_4=H$, $R_2+R_3=$—$OCH_2O$—, R=n-propyl and $R_5+R_6=$piperidinyl The title compound was prepared from 3,4-methylenedioxybenzaldehyde of formula 2 (5.0 g, 33 mmol) by subjecting it to Grignard's reaction with 1-n-bromobutane by the method described in example 1(i) to give 1-(3,4-methylenedioxyphenyl)-n-pentanol of formula 3 (6.6 g, 96%). The secondary alcohol (6.2 g, 30 mmol) was subjected to Vilsmeier reaction with dimethyl formamide-phosphorous oxychloride as described in example 1 (ii) to furnish 2-formyl-1-(3,4-methylenedioxyphenyl)-1-pentene (4.2 g, 67%). The resulting aldehyde (3.5 g, 16 mmol) was subjected to Wittig reaction as described in example 1 (iii) followed by saponification to produce 5-(3,4-methylenedioxyphenyl)-4-n-propyl-2E,4E-pentadienoic acid (3.0 g, 65%). The pentadienoic acid (0.52 g, 2.0 mmol) after acid chloride formation with thionyl chloride, and reaction with piperidine was purified by column chromatography on silica gel to give 4-n-propyl-5-(3,4-methylenedioxyphenyl)-2E,4E-pentadienoic acid piperidine amide of formula 1a (0.84 g, 60%).

Example 5

Synthesis of 4-ethyl-5-(3,4-dimethoxyphenyl)-2E,4E-pentadienoic acid piperidide of formula 1a where $R_1=R_4=H$; $R_2=R_3=$—$OCH_3$, $R=C_2H_5$ and $H_5+R_6=$piperidinyl The title compound was prepared from 3,4-dimethoxybenzaldehyde (10.0 g, 60 mmol) of formula 2 by subjecting it to Grignard's reaction with 1-n-bromopropane by the method described in example 1(i) to give 1-(3,4-dimethoxyphenyl)-n-butanol (12.2 g, 97%) of formula 3. The secondary alcohol (6.5 g, 31 mmol) was subjected to Vilsmeier reaction with dimethyl formamide-phosphorous oxychloride as described in example 1 (ii) to furnish 2-formyl-1-(3,4-dimethoxyphenyl)-1-butene (5.5 g, 66%). The resulting aldehyde (5.0 g, 22.5 mmol) was subjected to Wittig reaction as described in example 1 (iii) followed by saponification to produce 5-(3,4-dimethoxyphenyl)-4-ethyl-2E,4E-pentadienoic acid (3.77 g, 65%). The pentadienoic acid (0.80 g, 3.0 mmol) after acid chloride formation with thionyl chloride, and reaction with piperidine was purified by column chromatography on silica gel to give 4-ethyl-5-(3,4-dimethoxyphenyl)-2E,4E-pentadienoic acid piperidine amide of formula 1a (0.90 g, 91%).

Example 6

Synthesis of 4-ethyl-5-(2,2-dimethyl-2H-benzopyran-6-yl)-2E,4E-pentadienoic acid piperidine amide of formula 1a where $R_1=R_4=H$; $R_2+R_3=$—$CH_2CH_2C(CH_3)_2O$—, $R=C_2H_5$ and $R_5+R_6=$piperidinyl The title compound was prepared from 6-formyl-2,2-dimethyl(2H)-benzopyran of formula 2 (4.5 g, 23 mmol) by subjecting it to Grignard's reaction as described in example 1 (i) with 1-n-bromopropane to give 1-(2,2-dimethyl-2H-benzopyran-6-yl)-n-butanol of formula 3 (5.1 g, yield 94.5%). The secondary alcohol (4.5 g, 20 mmol) subjected to Vilsmeier reaction with dimethyl formamide-phosphorous oxychloride as described in example 1 (ii) to furnish 2-formyl-1-(3,4-ethylenedioxyphenyl)-1-butene (3.2 g, 66%). The resulting aldehyde (3.0 g, 12 mmol) was subjected to Wittig reaction as described in example 1 (iii) followed by saponification to produce 5-(2,2-dimethyl-2H-benzopyran-6-yl)-4-ethyl-2E,4E-pentadienoic acid (2.4 g, 70%). The pentadienoic acid (1.2 g, 4.0 mmol) after acid chloride formation with thionyl chloride, and reaction with piperidine was purified by column chromatography on silica gel to give 4-ethyl-5-(2,2-dimethyl-2H-benzopyran-6-yl)- -2E,4E-pentadienoic acid piperidine amide of formula 1a (1.1 g, 80%).

Example 7

Synthesis of 4-ethyl-5-(3,4-ethylenedioxyphenyl)-2E,4E-pentadienoic acid piperidine amide of formula 1a where $R_1=R_4=H$; $R_2+R_3=$—$OCH_2CH_2O$—, $R=C_2H_5$ and $R_5+R_6=$piperidinyl The title compound was prepared from 3,4-ethylenedioxybenzaldehyde of formula 2 (8.0 g, 47 mmol) by subjecting it to Grignard's reaction with 1-n-bromopropane by the method described in example 1(i) give 1-(3,4-ethylenedioxyphenyl)-butan-1-ol (9.4 g, 96%). The secondary alcohol (8.5 g, 20 mmol) was subjected to Vilsmeier reaction with dimethyl formamide-phosphorous oxychloride as described in example 1 (ii) to furnish 2-formyl-1-(3,4-ethylenedioxyphenyl)-1-butene (6.1 g, 70%). The resulting aldehyde (4.5 g, 20 mmol) was subjected to Wittig reaction as described in example 1 (iii) followed by saponification to produce 5-(3,4-ethylenedioxyphenyl)-4-ethyl-2E,4E-pentadienoic acid (4.0 g, 77%). The pentadienoic acid (0.8 g, 3.0 mmol) after acid chloride formation with thionyl chloride, and reaction with piperidine was purified by column chromatography on silica gel to give 4-ethyl-5-(3,4-ethylenedioxyphenyl)-2E,4E-pentadienoic acid piperidine amide of formula 1a (0.88 g, 90%).

Example 8

Syntheses of 4-ethyl-5-(3,4-methylenedioxyphenyl)-2E,4Z-pentadienoic acid piperidine amide of formula 1a where $R_1=R_4=H$, $R_2+R_3=-OCH_2O-$, R=ethyl and $R_5+R_6=$piperidinyl The title compound was prepared from 3,4-methylenedioxybenzaldehyde of formula 2 (7.5 g, 33 mmol) by subjecting it to Grignard's reaction with 1-n-bromopropane by the method described in example 1(i) to give 1-(3,4-methylenedioxyphenyl)-n-butanol of formula 3 (9.4 g, 97%). The secondary alcohol (7.8 g, 40 mmol) was subjected to Vilsmeier reaction with dimethyl formamide-phosphorous oxychloride as described in example 1 (ii) to furnish 2-formyl-1-(3,4-methylenedioxyphenyl)-1-butene (5.7 g, 70%). The resulting aldehyde (3.5 g, 16 mmol) after dissolution in dimethyl formamide (30 ml) was subjected to Wittig reaction as described in example 1 (iii) followed by saponification to produce a mixture of 5-(3,4-methylenedioxyphenyl)-4-ethyl-2E,4E-pentadienoic acid and 5-(3,4-methylenedioxyphenyl)-4-ethyl-2E,4Z-pentadienoic acid (4.8 g, 70%) in ratio of 4:1. The pentadienoic acid as geometrical isomeric mixture after acid chloride formation with thionyl chloride, and reaction with piperidine was purified by column chromatography on silica gel to give 5-(3,4-methylenedioxyphenyl)-ethyl-2E,4Z-pentadienoic acid piperidine amide of formula 1a (1.0 g, 20%).

Example 9

Syntheses of 4-ethyl-5-(3,4-methylenedioxyphenyl)-2E-pentenoic acid piperidine amide of formula 1b where $R_1=R_4=H$, $R_2+R_3=-OCH_2O-$, R=ethyl and $R_5+R_6=$piperidinyl The title compound was prepared from 3,4-methylenedioxybenzaldehyde of formula 2 (7.5 g, 50 mmol) by subjecting it to Grignard's reaction with 1-bromopropane by the method described in example 1(i) to give 1-(3,4-methylenedioxyphenyl)-n-butanol of formula 3 (9.4 g, 97%). The secondary alcohol (7.8 g, 40 mmol) was subjected to Vilsmeier reaction with dimethyl formamide-phosphorous oxychloride as described in example 1 (ii) to furnish 2-formyl-1-(3,4-methylenedioxyphenyl)-1-butene (5.0 g, 67%). The resulting aldehyde (2.0 g, 10 mmol) was hydrogenated in presence of Pd/C in methanol to furnish after purification corresponding dihydro derivative (1.0 g, 50%) of formula 5. The dihydro derivative of formula 5 was subjected to Wittig reaction as described in example 1 (iii) followed by saponification to produce 5-(3,4-methylenedioxyphenyl)-4-ethyl-4E-pentenoic acid (0.8 g, 86%) of formula 7. The pentenoic acid (0.75 g, 3.0 mmol) of formula 9 after acid chloride formation with thionyl chloride, and reaction with piperidine was purified by column chromatography on silica gel to give 5-(3,4-methylenedioxyphenyl)-4-ethyl-2E-pentenoic acid piperidine amide of formula 1b (0.8 g, 86%).

Example 10

Decrease in the MICs of Amikacin Against *Staphylococcus aureus*, MRSA When Used in Combination with Compound of Formula 1a Where $R_1=R_4=H$; $R_2+R_3=-OCH_2O-$, $R=C_2H_5$ and $R_5+12_4=$piperidinyl Minimum Inhibitory Concentration (MIC) of Amikacin alone and in combination with the above mentioned potentiator was performed against *Staphylococcus aureus* species, using method described in the study design. Four-fold reduction in MIC of Amikacin was observed in combination with the potentiator (Table 1).

Example 11

Decrease in the MICs of Ciprofloxacin against *Staphylococcus aureus*, MRSA and *Staphylococcus hemolyticus* Used in Combination with Compound of Formula 1a where $R_1=R_4=H$; $R_2+R_3=-OCH_2O-$, $R=C_2H_5$ and $R_5+R_6=$piperidinyl Minimum Inhibitory Concentration (MIC) of ciprofloxacin alone and in combination with the above-mentioned potentiator was performed against bacterial species, using method described in the study design. Two to more than eight fold reductions in MIC of ciprofloxacin was observed in combination with the potentiator (Table-2).

Example 12

Decrease in the MICs of Rifampicin Against *M. tuberculosis*, *M. avium* and *M. intracellure* When Used in Combination with Compound of Formula 1a Where $R_1=R_4=H$; $R_2+R_3=-OCH_2O-$, $R=C_2H_5$ and $R_5+R_6=$piperidinyl Minimum Inhibitory Concentration (MIC) of rifampicin alone and in combination with the above-mentioned potentiator was performed against Mycobacterial species, using method described in the study design. Two-fold reduction in MIC of rifampicin was observed in combination with the potentiator (Table 3).

Example 13

Decrease in the MICs of Mupirocin Against *Staphylococcus aureus*, and MRSA Used in Combination with Compound of Formula 1a Where $R_1=R_4=H$; $R_2+R_3=-OCH_2O-$, $R=C_2H_5$ and $R_5+R_6=$piperidinyl Minimum Inhibitory Concentration (MIC) of mupirocin alone and in combination with the above-mentioned potentiator was performed against bacterial species, using method described in the study design. Two to more than four fold reductions in MIC of mupirocin was observed in combination with the potentiator (Table-4).

Example 14

Comparison of the Potentiating Activity of Compound of Formula 1a ($R_1=R_4=H$; $R_2+R_3=-OCH_2O-$, $R=C_2H_5$ and $R_5+R_6=$piperidinyl) with Piperine in Reducing the MIC of Antibacterial Agents Against *S. aureus* 29213, MRSA and *M. tuberculosis* $H_{37}Rv$ Minimum Inhibitory Concentration (MIC) of antibacterial agents (Ciprofloxacin, Amikacin, Rifampicin and Mupirocin) was determined alone and in combination with compound of formula (1a). MIC of the abovementioned antibacterial agents was also determined in combination with piperine. The result revealed that compound of formula 1 was four times more potent than piperine in reducing the MICs of the antibacterial agents (Table-5 A & B)

Example 15

Reduction in the Dose Requirement of Ciprofloxacin When Used in Combination with Compound of Formula 1a (where $R_1=R_4=H$; $R_2+R_3=$—OCH$_2$O—, $R=C_2H_5$ and $R_5+R_5+R_6=$piperidinyl) in Systemic Infection Model of Mice

The study was conducted to see the in vivo response of ciprofloxacin in combination with the above-mentioned potentiator. The Swiss albino mice were infected intravenously with *Staphylococcus aureus* ATCC 29213 ($10^7$ CFU/mouse). The infected mice were divided in groups and each group consisted of 6 mice. The treatment consisted of one dose i.e. 5 or 10 or 20 mg/kg immediately after the infection followed by the next dose after a gap of 6 hrs. The result was recorded as number of survivals each day. The mice were observed for seven days and $ED_{50}$ was determined after seven days of observation. The $ED_{50}$ for ciprofloxacin was 9.2 mg/kg and in combination with the potentiator the $ED_{50}$ for ciprofloxacin was reduced to 5.86 mg/kg.

Example 16

Reduction in the Dose Requirement of Mupirocin when Used in Combination with Compound of Formula 1a where $R_1=R_4=H$; $R_2+R_3=$—OCH$_2$O—, $R=C_2H_5$ and $R_5+R_6=$piperidinyl

The study was conducted to see the in vivo response of Mupirocin in combination with the above-mentioned potentiator. Wound area of 1.5 cm×1.5 cm was created on the skin of mice by abrasion with sand paper. An inoculum of $10^8$ CFU/ml of MRSA was applied on to this wound area. The wound was treated for five days (two applications a day) with mupirocin cream and the other group with a formulation of mupirocin at $\frac{1}{4}^{th}$ concentration and compound of formula 1a. The combination of mupirocin with compound of formula-1a showed better wound healing. (Table-6).

Example 17

**Increased Accumulation and Decreased Efflux of Ethidium Bromide by Compound of Formula 1a where $R_1=R_4=H$; $R_2+R_3=$—OCH$_2$O—, $R=C_2H_5$ and $R_5+R_6=$piperidinyl in *Staphylococcus aureus* (wild type) and Ciprofloxacin mutant (Cip$^R$)**

Measurement of the level of ethidium bromide accumulation and efflux in *S. aureus* ATCC 29213 (wild strain) and strain CIP$^r$-1 (ciprofloxacin-selected mutant) was based on a previously described method (Brenwald et. al, *Antimicrobial Agents and Chemotherapy* 1998; 42(8): 2032-2035). Briefly, for measurement of the level of accumulation, both the bacterial strains were grown overnight on Trypticase Soya Agar. Bacterial suspensions were prepared at an optical density at 550 nm of 0.2 in uptake buffer (NaCl, 110 mM; KCl, 7 mM; NH4Cl, 50 mM; Na2HPO4, 0.4 mM; Tris base, 52 mM; glucose, 0.2% adjusted to pH 7.5 with HCl) and were then exposed to ethidium bromide at a concentration of 2 μg/ml. The increase in fluorescence as ethidium bromide entered the cells was recorded fluorometrically with a Perkin-Elmer model LS50 spectrofluorimeter (excitation λ, 530 nm; emission λ, 600 nm) at 30° C. The effect of compound of formula 1a where $R_1=R_4=H$; $R_2+R_3=$—OCH$_2$O—, $R=C_2H_5$ and $R_5+R_6=$piperidinyl on the level of accumulation was determined in a similar way, except that compound of formula 1a was added to the uptake buffer at a concentration of 25 μg/ml (FIG.—IA)

For determining ethidium bromide loss, bacterial suspensions were prepared as described above and were exposed to ethidium bromide (2 μg/ml) in the presence of compound of formula 1a (25 μg/ml) for 30 min at 37° C. The cells were then pelleted by centrifugation and were resuspended in fresh uptake buffer. The loss of ethidium bromide from the cells was measured as a decrease in fluorescence (FIG.—IB)

Example 18

List of Drugs Cited in Accompanying Table 7 as Some of the Examples for the Purpose of the Present Invention

Table 7 summarises the MIC results obtained with anti infective drugs when tested alone and in combination with compounds of the formula 1a, 1b, 1c. The % decrease in MIC obtained in the combination is depicted in the table no. 7.

TABLE 1

MICs of Amikacin alone and in combination with compound of formula 1a where $R_1 = R_4 = H$; $R_2 + R_3 = $ —OCH$_2$O—, $R = C_2H_5$ and $R_5 + R_6 = $ piperidinyl (Figures in bold face show reduction in MIC)

| Compound of formula 1a Conc (μg/ml) | MIC (μg/ml) of Amikacin for gram positive isolates | | | | |
|---|---|---|---|---|---|
| | *S aureus* | | | *S epidermidis* | |
| | ATCC 29213 | MRSA 33 | MRSA 450 | ATCC 12228 | *B cereus* RRL 101 |
| — | 2.0 | 8.0 | 16 | 1.0 | 1.0 |
| 6.25 | 1.0 | 8.0 | 8.0 | 0.5 | 1.0 |
| 12.5 | 1.0 | 8.0 | 8.0 | 0.5 | 0.25 |
| 25.0 | 0.5 | 4.0 | 4.0 | 0.25 | 0.25 |
| 50.0 | 0.25 | 2.0 | 4.0 | 0.25 | 0.25 |

TABLE 2

MICs of Ciprofloxacin alone and in combination with compound of formula 1a where $R_1 = R_4 = H$; $R_2 + R_3 = $ —OCH$_2$O—, $R = C_2H_5$ and $R_5 + R_6 = $ piperidinyl. (Figures in bold face show reduction in MIC)

| Compound of formula 1a Conc (μg/ml) | MIC (μg/ml) Ciprofloxacin for gram positive isolates | | | | |
|---|---|---|---|---|---|
| | *S aureus* | | | *S epidermidis* | |
| | ATCC 29213 | MRSA 33 | MRSA 450 | ATCC 12228 | *B cereus* RRL 101 |
| — | 0.25 | 32 | 32 | 0.12 | 0.12 |
| 6.25 | 0.12 | 32 | 32 | 0.12 | 0.12 |
| 12.5 | 0.06 | 16 | 16 | 0.06 | 0.06 |
| 25.0 | 0.06 | 16 | 16 | 0.03 | 0.03 |
| 50.0 | 0.06 | 16 | 16 | 0.03 | 0.03 |

TABLE 3

MIC of Rifampicin alone and in combination with compound of formula 1a where $R_1 = R_4 = H$; $R_2 + R_3 = -OCH_2O-$, $R = C_2H_5$ and $R_5 + R_6 =$ pyrrolidinyl. (Figures in bold face show reduction in MIC)

| Compound of formula 1a Conc (µg/ml) | MIC (µg/ml) for Mycobacterial isolates ||||| 
|---|---|---|---|---|---|
| | *M. tuberculosis* H37Rv | *M. tuberculosis* 611 | *M. tuberculosis* 615 | *M. avium* ATCC 49601 | *M. intracellure* ATCC 13950 |
| — | 0.12 | 0.06 | 0.06 | 2.0 | 2.0 |
| 0.09 | 0.03 | 0.03 | 0.03 | 2.0 | 2.0 |
| 0.78 | 0.03 | 0.03 | 0.03 | 2.0 | 1.0 |
| 6.25 | 0.03 | 0.03 | 0.03 | 1.0 | 1.0 |
| 50.0 | 0.03 | 0.03 | 0.03 | 1.0 | 1.0 |

TABLE 4

MICs of Mupirocin alone and in combination with compound of formula 1a where $R_1 = R_4 = H$; $R_2 + R_3 = -OCH_2O-$, $R = C_2H_5$ and $R_5 + R_6 =$ piperidinyl. (Figures in bold face show reduction in MIC)

| Compound of formula 1a Conc (µg/ml) | MIC (µg/ml) for *S aureus* isolates ||||
|---|---|---|---|---|
| | ATCC 29213 | MRSA 15187 | MRSA 33 | MRSA 450 |
| — | 0.12 | 0.25 | 0.12 | 0.25 |
| 3.12 | 0.12 | 0.25 | 0.12 | 0.25 |
| 6.25 | 0.12 | 0.25 | 0.12 | 0.25 |
| 12.5 | 0.06 | 0.12 | 0.06 | 0.12 |
| 25.0 | 0.06 | 0.06 | 0.03 | 0.12 |
| 50.0 | 0.03 | 0.06 | 0.03 | 0.06 |

TABLE 5A

MIC of antibacterial agents alone and in combination with compound of formula 1a $R_1 = R_4 = H$; $R_2 + R_3 = -OCH_2O-$, $R = C_2H_5$ and $R_5 + R_6 =$ piperidinyl. (Figures in bold face show reduction in MIC)

| Organism | Compound of formula 1a (µg/ml) | MIC (µg/ml) ||||
|---|---|---|---|---|---|
| | | Ciprofloxacin | Amikacin | Rifampicin | Mupirocin |
| *S aureus* ATCC 29213 | — | 0.25 | 2.0 | | 0.12 |
| | +6.25 | 0.12 | 1.0 | | 0.12 |
| | +12.5 | 0.06 | 1.0 | | 0.06 |
| | +25.0 | 0.06 | 0.5 | | 0.06 |
| | +50.0 | 0.03 | 0.12 | | 0.06 |
| MRSA | — | 32 | 4.0 | | 0.12 |
| | +6.25 | 32 | 4.0 | | 0.12 |
| | +12.5 | 16 | 4.0 | | 0.06 |
| | +25.0 | 16 | 4.0 | | 0.06 |
| | +50.0 | 8.0 | 4.0 | | 0.03 |
| *M tuberculosis* H37Rv | — | | | 0.12 | |
| | +6.25 | | | 0.12 | |
| | +12.5 | | | 0.06 | |
| | +25.0 | | | 0.015 | |

TABLE 5B

MIC of antibacterial agents alone and in combination with compound of formula 1a $R_1 = R_4 = H$; $R_2 + R_3 = -OCH_2O-$, $R = C_2H_5$ and $R_5 + R_6 =$ piperidinyl. (Figures in bold face show reduction in MIC)

| Organism | Piperine (µg/ml) | MIC (µg/ml) ||||
|---|---|---|---|---|---|
| | | Ciprofloxacin | Amikacin | Rifampicin | Mupirocin |
| *S aureus* ATCC 29213 | — | 0.25 | 2.0 | | 0.12 |
| | +6.25 | 0.25 | 2.0 | | 0.12 |
| | +12.5 | 0.25 | 1.0 | | 0.12 |
| | +25.0 | 0.12 | 0.5 | | 0.06 |
| | +50.0 | 0.12 | 0.25 | | 0.06 |
| MRSA | — | 32 | 4.0 | | 0.12 |
| | +6.25 | 32 | 4.0 | | 0.12 |
| | +12.5 | 32 | 4.0 | | 0.12 |
| | +25.0 | 32 | 4.0 | | 0.06 |
| | +50.0 | 16 | 4.0 | | 0.06 |
| MRSA | — | 32 | 4.0 | | 0.12 |
| | +6.25 | 32 | 4.0 | | 0.12 |
| | +12.5 | 32 | 4.0 | | 0.12 |
| | +25.0 | 32 | 4.0 | | 0.06 |
| | +50.0 | 16 | 4.0 | | 0.06 |
| *M tuberculosis* H37Rv | — | | | 0.12 | |
| | +6.25 | | | 0.12 | |
| | +12.5 | | | 0.06 | |
| | +25.0 | | | 0.06 | |

TABLE 6

Treatment of wound infection with mupirocin in combination with compound of formula 1a where $R_1 = R_4 = H$; $R_2 + R_3 = -OCH_2O-$, $R = C_2H_5$ and $R_5 + R_6 =$ piperidinyl

| Treatment Groups | Growth | Mean CFU |
|---|---|---|
| Control | 5/5 | $1.7 \times 10^7$ |
| 2% Mupirocin | 3/5 | $1.08 \times 10^4$ |
| 0.5% Mupirocin + 0.5% compound of formula 1 | 0/5 | — |
| 0.5% Mupirocin + 0.25% compound of formula 1 | 1/5 | $4.0 \times 10^3$ |
| 0.25% Mupirocin + 0.25% compound of formula 1 | 4/5 | $2.5 \times 10^4$ |

TABLE 7

MICs of the anti infective drugs alone and in combination with potentiators

| | | Potentiator (Structure Formula 1a) | | | MIC (μg/ml) | | % decrease |
|---|---|---|---|---|---|---|---|
| Drugs | Organisms | R | $R_1, R_2, R_3, R_4$ | $R_5, R_6$ | Drug alone | Drug + potentiator | in MIC |
| Ciprofloxacin | Gm +ve bacteria | $C_2H_5$ | $R_2 + R_3 =$ OCH$_2$O— $R_1 = R_4 = H$ | $R_5 + R_6 =$ Piperidinyl | 0.12-32 | 0.06-8 | 50-76 |
| | Gm −ve bacteria | | | | 0.03-0.5 | 0.03-0.25 | 0-50 |
| | M. tb | | | | 0.5-1 | 0.25-0.5 | 50 |
| Ofloxacin | Gm +ve bacteria | | | | 012-32 | 0.06-8 | 50-76 |
| | Gm −ve bacteria | | | | 0.06-32 | 0.03-16 | 50 |
| | M. tb | | | | 0.5-2.5 | 0.5-1.25 | 0-50 |
| Norfloxacin | Gm +ve bacteria | | | | 0.12-32 | 0.06-4 | 50-97 |
| | Gm −ve bacteria | | | | 0.03-64 | 0.03-32 | 0-50 |
| Amikacin | Gm +ve bacteria | | | | | | |
| | Gm −ve bacteria | | | | | | |
| | M. tb | | | | | | |
| Gentamicin | Gm +ve bacteria | | | | | | |
| | Gm −ve bacteria | | | | | | |
| Streptomycin | M. tb | | | | | | |
| Rifampicin | M. tb | | | | | | |
| Mupirocin | Gm +ve bacteria | | | | | | |
| Ciprofloxacin | Gm +ve bacteria | $C_2H_5$ | $R_2 + R_3 =$ OCH$_2$O— $R_1 = R_4 = H$ | $R_5 + R_6 =$ 4-hydroxy piperidinyl | 0.03-0.5 | 0.03-0.25 | 0-50 |
| Ciprofloxacin | Gm +ve bacteria | $C_2H_5$ | $R_2 + R_3 =$ OCH$_2$O— $R_1 = H, R_4 = NO_2$ | $R_5 + R_6 =$ Piperidinyl | 0.03-0.5 | 0.03-0.25 | 0-50 |
| Ciprofloxacin | Gm +ve bacteria | $C_2H_5$ | $R_2 + R_3 =$ OCH$_3$— $R_1 = R_4 = H$ | $R_5 + R_6 =$ Piperidinyl | 0.12-32 | 0.06-8 | 50-76 |
| | Gm −ve bacteria | | | | 0.03-0.5 | 0.03-0.25 | 0-50 |
| | M. tb | | | | 0.5-1 | 0.25-0.5 | 50 |
| Ciprofloxacin | Gm +ve bacteria | $C_4H_9$ | $R_2 + R_3 =$ OCH$_3$— $R_1 = R_4 = H$ | $R_5 + R_6 =$ Piperidine | 0.12-32 | 0.06-8 | 50-76 |
| | Gm −ve bacteria | | | | 0.03-0.5 | 0.03-0.25 | 0-50 |
| | M. tb | | | | 0.5-1 | 0.25-0.5 | 50 |
| Ciprofloxacin | Gm +ve bacteria | $CH_3$ | $R_2 + R_3 =$ OCH$_3$— $R_1 = R_4 = H$ | $R_5 =$ 1-(4-bromophenyl)ethylaminyl $R_6 = H$ | 0.12-32 | 0.06-8 | 50-76 |
| | Gm −ve bacteria | | | | 0.03-0.5 | 0.03-0.25 | 0-50 |
| | M. tb | | | | 0.5-1 | 0.25-0.5 | 50 |
| Ciprofloxacin | Gm +ve bacteria | $CH_3$ | $R_2 + R_3 =$ OCH$_3$— $R_1 = R_4 = H$ | $R_5 = R_6 = C_2H_5$ | 0.12-0.5 | 0.06-0.12 | 50-76 |
| Ciprofloxacin | Gm +ve bacteria | $CH_3$ | $R_2 + R_3 =$ OCH$_2$O— $R_1 = R_4 = H$ | $R_5 + R_6 =$ N-methyl piperazine | 0.12-0.5 | 0.06-0.12 | 50-76 |
| Ciprofloxacin | Gm +ve bacteria | $CH_3$ | 4-methoxy | $R_5 + R_6 =$ N-methyl piperidinyl | 0.12-32 | 0.06-16 | 50 |
| | Gm −ve bacteria | | | | 0.03-0.5 | 0.03-0.25 | 0-50 |
| | M. tb | | | | 0.5-1 | 0.25-0.5 | 50 |
| Ciprofloxacin | Gm +ve bacteria | $C_2H_5$ | $R_2 + R_3 =$ OCH$_2$O— $R_1 = R_4 = H$ | $R_5 = CH_2COOH$ $R_6 = H$ | 0.03-0.5 | 0.03-0.25 | 0-50 |
| Ciprofloxacin | Gm +ve bacteria | StructureFormula 1c $C_2H_5$ | $R_2 + R_3 =$ OCH$_2$O— $R_1 = R_4 = H$ | $R_5 + R_6 =$ Piperidinyl | 0.03-0.5 | 0.03-0.25 | 0-50 |

Gm +ve = Gram positive
Gm −ve = Gram negative
*M. tb* = *Mycobacterium tuberculosis*

What is claimed is:

1. A method for inhibiting growth of a bacterial cell that employs an efflux pump resistance mechanism, comprising administering to a subject in need thereof a pharmaceutical composition comprising an effective amount of a potentiating compound of general formula 1 a-c including geometrical isomers and/or salts thereof:

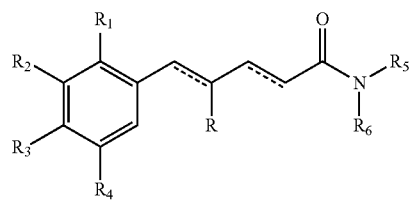

1a-c wherein R represents normal or branched chain $C_1$ to $C_{10}$ alkyl group and $R_1$, $R_2$ and $R_3$ independently represent hydrogen, methoxyl, hydroxyl, halogen, or nitro; or where $R_2$ and $R_3$ together $(R_2+R_3)$ represent —OCH$_2$O—, —OCH$_2$CH$_2$O—, —CH$_2$CH$_2$CH$_2$O—, or —CH$_2$CH$_2$C(CH$_3$)$_2$O—; $R_4$ represents hydrogen or methoxyl; $R_5$ represents hydrogen, normal or branched chain $C_1$ to $C_8$ alkyl, phenyl or benzyl; and $R_6$ represents hydrogen, or $C_1$ to $C_8$ normal or branched chain alkyl group; or where $NR_5R_6$ together $(R_5+R_6)$ represent an amino acid radical or a heterocyclic amine radical; and where dotted lines indicate the presence of double and/or single bonds.

2. The method of claim 1 where the potentiating compound comprises a compound of formula 1 a:

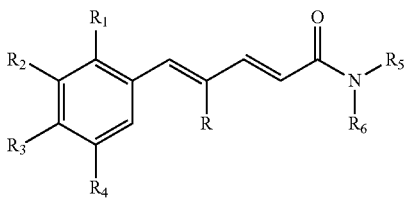

including geometrical isomers and/or salts thereof.

3. The method of claim 1 where the potentiating compound comprises a compound of formula 1 b:

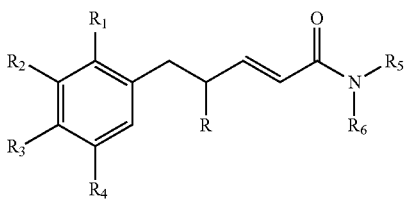

including geometrical isomers and/or salts thereof.

4. The method of claim 1 where the potentiating compound comprises a compound of formula 1 c:

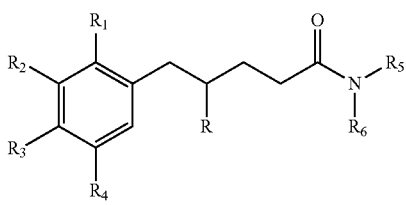

including geometrical isomers and/or salts thereof.

5. The method of claim 1, wherein the potentiating compound is in the form of a pharmaceutically acceptable salt selected from hydrochloride, acetate, succinate, and maleate.

6. The method of claim 1 wherein $NR_5R_6$ together ($R_5+R_6$) represent an amino acid radical comprising at least one of alaninyl, leucinyl, phenylalaninyl, tyrosinyl, glycylglycinyl, alanylalaninyl or prolinyl; or a heterocyclic amine radical comprising at least one of piperidinyl, pyrrolidinyl, morpholinyl, piperazinyl, N-methylpiperazinyl, pyrrolyl, imidazolyl, or oxazolyl.

7. The method of claim 1, wherein the bacterial cell comprises a gram positive bacterium.

8. The method of claim 7 wherein the gram positive bacterium comprises at least one of *Staphylococcus species* and *Bacillus* species.

9. The method as claimed in claim 1, wherein the bacterial cell comprises a gram negative bacterium.

10. The method of claim 9 wherein the gram negative bacterium comprises at least one of *Pseudomonas species, E coli* and *Salmonella* species.

11. The method of claim 1, wherein the bacterial cell comprises *mycobacterium* species.

12. The method of claim 1, wherein the composition further comprises an effective amount of an anti-infective drug.

13. The method of claim 1, wherein the composition further comprises at least one carrier, diluent, or pharmaceutically acceptable excipient.

14. A method of treating an infection comprising administering to a subject in need of such treatment a therapeutically effective amount of a pharmaceutical composition comprising an effective amount of a potentiating compound of general formula 1 a-c including geometrical isomers and/or salts thereof

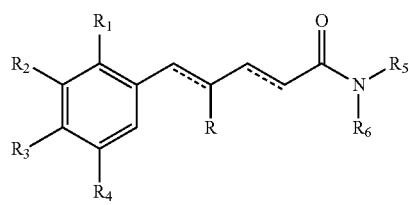

wherein R represents normal or branched chain $C_1$ to $C_{10}$ alkyl group and $R_1$, $R_2$ and $R_3$ independently represent hydrogen, methoxyl, hydroxyl, halogen, or nitro; or where $R_2$ and $R_3$ together ($R_2+R_3$) represent —$OCH_2O$—, —$OCH_2CH_2O$—, —$CH_2CH_2CH_2O$—, or —$CH_2CH_2C(CH_3)_2O$—; $R_4$ represents hydrogen or methoxyl; $R_5$ represents hydrogen, normal or branched chain $C_1$ to $C_8$ alkyl, phenyl or benzyl; and $R_6$ represents hydrogen, or $C_1$ to $C_8$ normal or branched chain alkyl group; or where $NR_5R_6$ together ($R_5+R_6$) represent an amino acid radical or a heterocyclic amine radical; and where dotted lines indicate the presence of double and/or single bonds.

15. The method of claim 14 where the potentiating compound comprises a compound of formula 1 a:

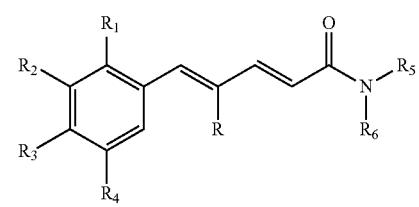

including geometrical isomers and/or salts thereof.

16. The method of claim 14 where the potentiating compound comprises a compound of formula 1 b:

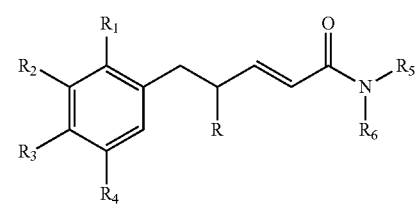

including geometrical isomers and/or salts thereof.

17. The method of claim 14 where the potentiating compound comprises a compound of formula 1 c:

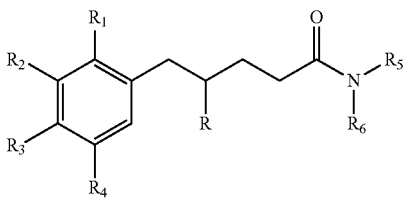

including geometrical isomers and/or salts thereof.

18. The method of claim 14, further comprising administering to the patient an effective amount of anti-infective drug.

19. The method of claim 14, wherein the pharmaceutical composition further comprises an effective amount of an anti-infective drug.

20. The method of claim 18, wherein the infection is caused by a bacterium that employs efflux pump resistance as a way of resistance to the anti-infective drug.

21. A method of potentiating bioefficacy of an anti-infective drug comprising administering to a patient in need thereof an effective amount of an anti-infective drug, and an effective potentiating amount of a potentiating compound of general formula 1 a-c including geometrical isomers and/or salts thereof:

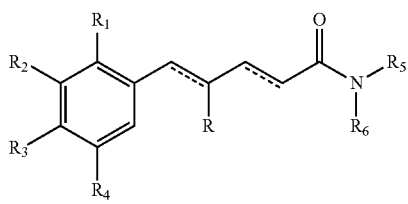

wherein R represents normal or branched chain $C_1$ to $C_{10}$ alkyl group and $R_1$, $R_2$ and $R_3$ independently represent hydrogen, methoxyl, hydroxyl, halogen, or nitro; or where $R_2$ and $R_3$ together $(R_2+R_3)$ represent —$OCH_2O$—, —$OCH_2CH_2O$—, —$CH_2CH_2CH_2O$—, or —$CH_2CH_2C(CH_3)_2O$—; $R_4$ represents hydrogen or methoxyl; $R_5$ represents hydrogen, normal or branched chain $C_1$ to $C_8$ alkyl, phenyl or benzyl; and $R_6$ represents hydrogen, or $C_1$ to $C_8$ normal or branched chain alkyl group; or where $NR_5R_6$ together $(R_5+R_6)$ represent an amino acid radical or a heterocyclic amine radical; and where dotted lines indicate the presence of double and/or single bonds.

22. A method of treating a subject having a bacterial infection, comprising administering to the subject in need thereof an effective amount of an anti-infective drug, and an effective potentiating amount of a potentiating compound, the potentiating compound comprising at least one of:

- 5-(3,4-methylenedioxyphenyl)-4-methyl-2E,4E-pentadienoic acid piperidide,
- 5-(3,4-methylenedioxyphenyl)-4-methyl-2E,4E-pentadienoic acid pyrrolidide,
- 5-(3,4-methylenedioxyphenyl)-4-methyl-2E,4E-pentadienoic acid -N,N-diethylamide,
- 5-(3,4-methylenedioxyphenyl)-4-methyl-2E,4E-pentadienoic acid- n-butylamide,
- 5-(3,4-methylenedioxyphenyl)-4-methyl-2E,4E-pentadienoic acid isobutylamide,
- 5-(3,4-methylenedioxyphenyl)-4-methyl-2E,4E-pentadienoic acid morpholide,
- 5-(3,4-methylenedioxyphenyl)-4-methyl-2E,4E-pentadienoic acid-N-methylpiperazide,
- 5-(3,4-methylenedioxyphenyl)-4-methyl-2E,4E-pentadienoic acid -4-hydroxypiperidide,
- 5-(3,4-methylenedioxyphenyl)-4-methyl-2E,4E-pentadienoic acid -1-(4-bromophenyl) ethylamide,
- 5-(3,4-methylenedioxyphenyl)-4-methyl-2E,4E-pentadienoic acid 2-(hydroxymethyl) propylamide,
- 5-(3,4-methylenedioxyphenyl)-4-methyl-2E,4E-pentadienoic acid n-octylamide,
- 5-(3,4-methylenedioxyphenyl)-4-ethyl-2E,4E-pentadienoic acid piperidide,
- 5-(3,4-methylenedioxyphenyl)-4-ethyl-2E,4E-pentadienoic acid pyrrolidide,
- 5-(3,4-methylenedioxyphenyl)-4-ethyl-2E,4E-pentadienoic acid-N,N-diethylamide,
- 5-(3,4-methylenedioxyphenyl)-4-ethyl-2E,4E- pentadienoic acid isobutylamide,
- 5-(3,4-methylenedioxyphenyl)-4-ethyl-2E,4E- pentadienoic acid -n-butylamide,
- 5-(3,4-methylenedioxyphenyl)-4-ethyl-2E,4E-pentadienoic acid morpholide,
- 5-(3,4-methylenedioxyphenyl)-4-ethyl-2E,4E-pentadienoic acid-N-methylpiperazide,
- 5-(3,4-methylenedioxyphenyl)-4-ethyl-2E,4E-pentadienoic acid -4-hydroxypiperidide,
- 5-(3,4-methylenedioxyphenyl)-4-ethyl-2E,4E- pentadienoic acid imidazolide,
- 5-(3,4-methylenedioxy-5-nitrophenyl)-4-ethyl-2E,4E-pentadienoic acid piperidide,
- 5-(3,4-methylenedioxyphenyl)-4-ethyl-2E,4E-pentadienoicacid-α-carbomethoxy methylamide,
- 5-(3,4-methylenedioxyphenyl)-4-ethyl-2E,4E-pentadienoic acid-(2-pyridyl)amide,
- 5-(3,4-methylenedioxyphenyl)-4-ethyl-2Z,4E-pentadienoic acid piperidide,
- 5-(3,4-methylenedioxyphenyl)-4-ethyl-2E,4Z-pentadienoic acid piperidide,
- 5-(3,4-methylenedioxyphenyl)-4-ethyl-2E-pentenoic acid piperidide,
- 5-(3,4-methylenedioxyphenyl)-4-ethyl-pentanoic acid piperidide,
- 5-(3,4-methylenedioxyphenyl)-4-methyl-pentanoic acid piperidide,
- 5-(3,4-methylenedioxyphenyl)-4-n-propyl-2E,4E-pentadienoic acid piperidide,
- 5-(3,4-methylenedioxyphenyl)-4-n-butyl-2E,4E-pentadienoic acid piperidide,
- 5-(3,4-methylenedioxyphenyl)-4-n-butyl-2E,4E-pentadienoic acid -4-hydroxy piperidide,
- 5-(3,4-methylenedioxyphenyl)-4-n-butyl-2E,4E-pentadienoic acid-4-N-methyl piperazide,
- 5-(4-methoxyphenyl)-4-methyl-2E,4E-pentadienoic acid piperidide,
- 5-(4-methoxyphenyl)-4-ethyl-2E,4E-pentadienoic acid piperidide,
- 5-(4-methoxyphenyl)-4-propyl-2E,4E-pentadienoic acid piperidide,
- 5-(4-methoxyphenyl)-4-n-butyl-2E,4E-pentadienoic acid piperidide,
- 5-(4-methoxyphenyl)-4-n-hexyl-2E,4E-pentadienoic acid piperidide,
- 5-(4-methoxyphenyl)-4-n-propyl-2E,4E-pentadienoic acid -N-methylpiperazide,
- 5-(3,4-dimethoxyphenyl)-4-ethyl-2E,4E-pentadienoic acid piperidide, 5-(3,4-ethylenedioxyphenyl)-4-ethyl-2E,4E-pentadienoic acid piperidide,
5-(3,4-dimethoxyphenyl)-4-ethyl-2E,4E-pentadienoic acid pyrrolidide,
5-(2,2-dimethyl-2H-benzopyran-6-yl)-4-ethyl-2E,4E-pentadienoic acid piperidide, or
5-(2,2-dimethyl-2H-benzopyran-6-yl)-4-ethyl-2E,4E-pentadienoic acid pyrrolidide;
including geometrical isomers and/or salts thereof.

\* \* \* \* \*